US005856122A

United States Patent [19]
Read et al.

[11] Patent Number: 5,856,122
[45] Date of Patent: Jan. 5, 1999

[54] MODIFICATION OF PERTUSSIS TOXIN

[75] Inventors: Randy J. Read; Penelope E. Stein, both of Edmonton; Stephen A. Cockle, Richmond Hill; Raymond P. Oomen, Tottenham; Sheena Loosmore, Aurora; Michel H. Klein, Willowdale; Glen D. Armstrong; Bart Hazes, both of Edmonton, all of Canada

[73] Assignee: University of Alberta, Edmonton, Canada

[21] Appl. No.: 292,968

[22] Filed: Aug. 22, 1994

Related U.S. Application Data

[63] Continuation-in-part of Ser. No. 251,121, May 31, 1994, abandoned, which is a continuation-in-part of Ser. No. 110,947, Aug. 24, 1993, abandoned.

[51] Int. Cl.$^6$ ................................................. C12P 21/02
[52] U.S. Cl. ................................................. 435/69.1; 435/15
[58] Field of Search ................................................. 435/15, 69.1

[56] References Cited

U.S. PATENT DOCUMENTS

| | | | |
|---|---|---|---|
| 4,883,761 | 11/1989 | Keith et al. | 435/252.33 |
| 5,427,788 | 6/1995 | Rappuoli et al. | 424/190.1 |

FOREIGN PATENT DOCUMENTS

| | | |
|---|---|---|
| A-0320866 | 6/1989 | European Pat. Off. . |
| A-0322115 | 6/1989 | European Pat. Off. . |
| A-0322533 | 7/1989 | European Pat. Off. . |
| A-0338566 | 10/1989 | European Pat. Off. . |
| A-0398322 | 11/1990 | European Pat. Off. . |
| A-0462534 | 12/1991 | European Pat. Off. . |
| WO-A-9219757 | 11/1989 | WIPO . |
| WA-A-9219646 | 11/1992 | WIPO . |

OTHER PUBLICATIONS

Locht et al., Inf. and Imm., vol. 55, No. 11, pp. 2546–2553 (1987).
Stein et al., Structure, vol. 2, No. 1, pp. 45–57 (1994).
Kaslow, H. and Burns, D. (1992), *FASEB J.* 6, 2684–2690.
Watkins, P. et al. (1984), *J. Biol. Chem.* 260, 13478–13482.
Lim, L.K. et al. (1985), *J. Biol Chem.* 260, 2585–2588.
Burns, D. and Manclark, C.C. (1986), *J. Biol. Chem.* 261. 4324–4327.
Moss, J., et al. (1986), *Biochemistry* 25, 2720–2725.
Armstrong, G., et al. (1988), *J. Biol. Chem.* 263, 8677–8684.
Witvliet, M., et al. (1989), *Infect. Immun.* 57, 3324–3330.
Saukkonen, K., et al (1992), *Proc. Natl Acad. Sci. U.S.A.* 89, 118–122.
Oda, M, et al. (1984), *J Infect. Dis.* 150, 823–833.
Sato, H. and Sato, Y (1984), *Infect. Immun.* 46, 415–421.
Halperin, S., et al. (1991), *J Infect. Dis.* 163, 355–361.
Olin, P. (1991), *Dev. Biol Stand.* 73, 33–36.
Zealey, G., et al. (1992), *Vaccine Research* 1, 413–427.
Pizza, M., et al. (1989), *Science* 246, 497–499.
Loosmore, S., et al. (1990), *Infect. Immun.* 58, 3653–3662.
Locht, C. and Keith, J. (1986), *Science* 232, 1258–1264.
Cieplak, W., et al. (1988), *Proc. Natl. Acad. Sci. USA* 85, 4667–4671.
Burnette, W., et al. (1988), *Science* 242, 72–74.
Kaslow, H., et al. (1992), *Vaccine Res.* 1, 47–54.
Cockle, S. (1989), *FEBS Letters* 249, 329–332.
Lobet, Y., et al. (1993), *J. Exp. Med.* 177, 79–87.
Loosmore, S., et al. (1993), *Infect. Immun.* 61, 2316–2324.
Choe, S., et al. (1992), *Nature* 357, 216–222.

(List continued on next page.)

*Primary Examiner*—Eric Grimes
*Attorney, Agent, or Firm*—Sim & McBurney

[57] ABSTRACT

The three-dimensional structure of crystalline pertussis holotoxin (PT) has been determined by X-ray crystallography. Crystal structures have also been determined for complexes of pertussis toxin with molecules relevant to the biological activity of PT. These three-dimensional structures were analyzed to identify functional amino acids appropriate for modification to alter the biological properties of PT. Similar procedures may be used to predict amino acids which contribute to the toxicity of the holotoxin, to produce immunoprotective, genetically-detoxified analogs of pertussis toxin.

5 Claims, 14 Drawing Sheets

OTHER PUBLICATIONS

Allured, V., et al. (1986), *Proc. Natl. Acad. Sci. U.S.A. 83*, 1320–1324.
Brandhuber, B. et al. (1988) *Proteins 3*, 146–154.
Sixma, T., et al. (1991), *Nature 351*, 371–377.
Sixma, T., et al. (1993), *J. Mol. Biol. 230*, 890–918.
Sixma, T., et al. (1993), *Biochemistry 32*, 191–198.
Stein, P., et al. (1992), *Nature 355*, 748–750.
Wout, J. et al. (1992), *Infect. Immun. 60*, 3303–3308.
Graf. R. et al. (1992) *Molec. Pharmacol.*, 42, 760–764.
Spangler, B., et al.(1988), *International Workshop on Bordetella pertussis*, Rocky Mountain Laboratories, Hamilton, Montana.
Raghavan, M., et al. (1990), *J. Molec. Biol. 213*, 411–414.
Sakabe, N. (1983), *J. Appl. Crystallogr. 16*, 542–547.
Hagashi, T. (1989), *J. Appl. Crystallogr. 22*, 9–18.
Sheldrick, G. (1991), in *Crystallographic Computing 5: From Chemistry to Biology* (eds Moras, D., et al.) pp. 145–157 (Oxford University Press, Oxford).
Otwinowski, Z. (1991), in *Isomorphous Replacement and Anomalous Scattering: Proceedings of the CCP4 Study Weekend 25–26 Jan. 1991* (eds Wolf, W., Evans, P. and Leslie, A.) pp. 80–86 (SERC, Daresbury Laboratory).
Colman, P. et al. (1976), in *Crystallographic Computing Techniques* (eds Ahmed, F., Huml, Y, and Sedlacek, B.) pp. 248–258 (Munksgaard, Copenhagen).
Read, R. and Schierbeek, K. (1988), *J Appl. Crystallogr. 21*, 490–495.
Podjarny, A. and Rees, B. (1991), in *Crystallographic Computing 5: From Chemistry to Biology* (eds Moras, D., Podjarny, A. and Thierry, J.) pp.361–372 (Oxford University Press, Oxford).
Pizza, M., et al. (1988), *Proc. Natl. Acad. sci. U.S.A. 85*, 7521–7525.
Barbieri, J. and Cortina, G. (1988), *Infect. Immun. 56*, 1934–1941.
Janin, J., et al. (1988), *J. Molec. Biol. 204*, 155–164.
Krueger, K., et al. (1991), *J. Biol. Chem. 266*, 8122–8128.
Murzin, A., (1993), *EMBO J.* 12 861–867.
Tamura, M., et al. (1982), *Biochemistry 21*, 5516–5522.
Jones, T., et al. (1991), *Acta Crystallogr. A47*, 110–119.
Brünger, A., et al. (1987), *Science 235*, 458–460.
Read, R. (1986), *Acta Crystallogr. A42*, 140–149.
Loosmore, S., et al. (1989), *Nucleic Acids Research 17*, 8365.
Morris, A., et al. (1992), *Proteins 12*, 345–364.
Kabsch, W. and Sander, C. (1983), *Biopolymers 22*, 2577–2637.
Weis, W., et al. (1991), *Science 254*, 1608–1615.
Weis, W., et al. (1992), *Nature 360*, 127–134.
Heerze, L., et al. (1992), *J. Biol. Chem. 267*, 25810–25815.
Wright, c. (1990), *J. Molec. Biol. 215*, 635–651.
Cortina, G. and Barbieri J. (1991), *J. Biol. Chem. 266*, 3022–3030.
Klein, P., et al. (1985), *Biochim. Biophys. Acta 815*, 468–476.
Breg, J. (1989) *Eur. J. Biochem. 178*, 727–739.
Shigeta R. (1994) *Acta Crystallagr D50*, 71–74.
Armstrong, G. and Peppler M. (1987), *Infect. Immun. 55*, 1294–1299.
Kaslow, H., et al. (1989), *J. Biol. Chem. 264*, 6386–6390.
Zealey, G. et al. (1992) *Appl. Environ. Microbiol. 58*, 208–214.
Krueger, K.M. and Barbieri, J.T. (1993), *J. Biol. Chem. 268*, 12570–12578.
Alberts et al., *Molecular Biology of the Cell*, Garland Publishing, NY, 1983, pp. 158–159.
Turner et al., Zbl. Bakteriol., Suppl. 23:302–303 (1992).
Sixma et al., Nature 355:561–564 (1992).
Schutt et al., Abstr. Pap. Am. Chem. Soc. 203: Medi 195 (1992).
Forest et al., Zbl. Bakteriol., Suppl. 23:304–305 (1992).

FIG. 4

```
            (1)           23          35           50                    (2)
PT    7  V Y R Y D S     F T A       H L          F V S T S S S R R Y T E     (7)
           (6)           22          44           59
LT    5  L Y R A D S     L M P       H A          Y V S T S L R S A H         (12)
          (11)          455                      468
ETA  438 G Y H G T F     V R A       - -          G F Y I A G D P A L A Y     (17)
          (16)           35
DT   19  S Y H G T K     I Q K       - -          G F Y S T D N K Y D A A
                                                                              (5)
          (3)                        98          128                          (10)
PT   84  F I G Y I Y E V R           Y G          S E Y L A H R     140  N I R R V  (10)
          (8)                        95          111                        (15)
LT   81  S T Y Y I Y V I A           F N          Q E V S A L G     123  Q I Y G W
          (13)         541                       552                         (20)
ETA  494 R N G A L L R V Y           A I          L E T I L G W     565  V V I P S
          (18)         136                       147
DT   76  K A G G V V K V T           L S          V E Y I N N W     160  S V E L E (1) = SER ID NO: 1        (8) = SER ID NO: 8        (15) = SER ID NO: 15
(2) = SER ID NO: 2        (9) = SER ID NO: 9        (16) = SER ID NO: 16
(3) = SER ID NO: 3       (10) = SER ID NO: 10       (17) = SER ID NO: 17
(4) = SER ID NO: 4       (11) = SER ID NO: 11       (18) = SER ID NO: 18
(5) = SER ID NO: 5       (12) = SER ID NO: 12       (19) = SER ID NO: 19
(6) = SER ID NO: 6       (13) = SER ID NO: 13       (20) = SER ID NO: 20
(7) = SER ID NO: 7       (14) = SER ID NO: 14
```

```
                   1                           7                                      17
VT                 TPDCVT--GKVEYTKYND---------------------DDTFTVKVG------
      96
S2     -QPATDHY-YS-NVTATRLLSST---------------------NSRLCAVFVRSGQ
      96                                                  116
S3     -QPAADHY-YS-KVTATRLLAST---------------------NSRLCAVFVRDGQ
      96                                                  116
S4     DVPYVLV-KT-NMVVTSVAMKPYEVTPTRMLVCGIAAKLGA
       1          11                                       27
S5     GLPTHL-YK-NFTVQELALKLKGK---NQEFCLTAFMSGR
      11          22                                       35
LT     -EYRNTQI-YTINDKILSYTESMAGK------REMVIITFKS-----
                  27                                       34

VT     -----------DKELFTNR---------------WNLQSLLLSAQIT
                  131                                     147
S2     ------VIGACTSPYDGKY---------------WSMYSRLRKMLYLIYVA
                  131                                     147
S3     ------VIGACASPYEGRY---------------RDMYDALRRLLYMIYMS
                  48                                       62
S4     AASSPDAHVPFCFGKDLKRPGS---------SPMEVMLRAVFMQ
                  38                                       54
S5     ------LVRACLSDAGHEHDT---------WFDTMLGFAISAYAL
                  46                                       66
LT     ------GETFQVEVPGSQHIDSQKKAIERMKDTLRITYLT
```

FIG.5A

```
VT  GMTV-TIKTNACHN------------GGGFSEVIFR                        69 (21)
                                   60
S2  GISV-RVHVSKEEQYYDYEDATFETYALTGISICNPGSSLC                  199 (22)
                                  183
S3  GLAV-RVHVSKEEQYYDYEDATFQTYALTGISICNPAASIC                  199 (23)
                                  183
S4  QRPL-RMFLGP-KQLTFEGK----PALELIRMVECSGKQDCP                 110 (24)
                                   94                 83
S5  KSRI-ALTVEDSPYPG---------TPGDLLELQICPLNGYCE                 99 (25)
                                                      93
LT  ETKIDKLCVWNNKT-------------PNSIAAISMKN                     103 (26)
```

(21) = SER ID NO: 21
(22) = SER ID NO: 22
(23) = SER ID NO: 23
(24) = SER ID NO: 24
(25) = SER ID NO: 25
(26) = SER ID NO: 26

FIG.5B

```
                          (27)                    (28)
S2    12         22       NKTRAL           38   SGDLQEYLRHVTR
      QIT        RC    25                     
S3    12         22       NGTRAL           33   NAELQTYLRQITP   (34)
      LFT        RC    25                                       
MBP   11         27       LRGTVA           40   NAEENKAIQEVAK   (40)
      FFV        LC    31

(30)                    (31)
S2    53         (29) 59  DGTYL            67   YGGVIKD         (32)
      SIFAL                                            TTFCIM   
S3    53         (35) 59  DGTYL            67   YGGIKD          (38)
      SIYGL                                            ETFCIT   
MBP   53         (41) 95  CVTIV           100   DNGLWND         (44)
      TSAFL                                            TAVCEF

(27) = SER ID NO: 27    (33) = SER ID NO: 33    (39) = SER ID NO: 39
(28) = SER ID NO: 28    (34) = SER ID NO: 34    (40) = SER ID NO: 40
(29) = SER ID NO: 29    (35) = SER ID NO: 35    (41) = SER ID NO: 41
(30) = SER ID NO: 30    (36) = SER ID NO: 36    (42) = SER ID NO: 42
(31) = SER ID NO: 31    (37) = SER ID NO: 37    (43) = SER ID NO: 43
(32) = SER ID NO: 32    (38) = SER ID NO: 38    (44) = SER ID NO: 44
```

MODIFICATION OF PERTUSSIS TOXIN

REFERENCE TO RELATED APPLICATION

This application is a continuation-in-part of U.S. patent application Ser. No. 08/251,121 filed May 31, 1994, now abandoned, which itself is a continuation-in-part of U.S. patent application Ser. No. 08/110,947 filed Aug. 24, 1993, now abandoned.

FIELD OF INVENTION

The present invention relates to a method for the prediction of functional amino acid residues in pertussis toxin, in order to manipulate the biological properties of the toxin, by determination of and examination of the crystal structures of the toxin alone and of complexes of the toxin with molecules relevant to its biological activity, including carbohydrate ligands, nucleotide effectors and substrates.

BACKGROUND OF THE INVENTION

Whooping cough, or pertussis, is a severe, highly contagious respiratory disease of infants and young children caused by infection with Bordetella pertussis. Owing to the many virulence factors associated with this organism, the pathogenesis of the disease is still not fully understood; however, it is generally recognized that major systemic effects are caused by pertussis toxin (PT). This material exhibits a wide range of biological activities, as illustrated by such alternative names as lymphocytosis-promoting factor, histamine-sensitizing factor and islet-activating protein (ref. 1- a list of the references appears at the end of the disclosure, each of which reference is incorporated herein by reference thereto).

PT is a 105-kDa exotoxin encoded by the tox operon and consists of five polypeptide subunits (S1 to S5) arranged in an A-B structure typical of some bacterial toxins. The S2, S3, S4, (two copies) and S5 subunits form a pentamer (the B oligomer) which when combined with the S1 subunit forms the holotoxin. S1 is an enzyme with ADP-ribosyltransferase and NAD-glycohydrolase activities. Its natural function is to catalyse the transfer of the ADP-ribose portion of nicotinamide adenine dinucleotide (NAD) to the membrane-bound guanine nucleotide-binding negative regulatory G-protein of adenylate cyclase ($G_i$), resulting in an increase in cyclic-AMP synthesis. This activity, which is the primary cause of PT toxicity, can be conveniently examined in vitro using as substrate the retinal G-protein transducin, which is a close analogue of $G_i$ (ref. 2). Such studies have demonstrated that PT is activated by adenine nucleotides, in particular by adenosine triphosphate (ATP) (refs. 3,4), while S1 itself is active only in the presence of thiols, such as dithiothreitol, that are required to reduce the single disulfide bond of S1 (ref. 5).

The B oligomer mediates the binding of the holotoxin to target cells and facilitates entry of the A protomer. PT has lectin-like properties, binding to glycoconjugates on many cell surfaces and to the oligosaccharide moieties of many serum glycoproteins (refs. 6,7). It has been reported that the toxin preferentially recognizes asparagine-linked oligosaccharide chains containing (2α-6)-linked sialic acid residues (ref. 6). However, a number of complex carbohydrate sequences are bound, and there is evidence that PT contains at least two binding domains with different specificities on each of the subunits S2 and S3 (refs. 7,8).

Several studies have indicated that PT is a major protective antigen against pertussis. Thus, purified, toxoided PT protects mice against both intracerebral and respiratory challenges with B. pertussis (refs. 9,10). Polyclonal anti-PT antisera and some anti-PT monoclonal antibodies also protect against challenge (refs. 9,10,11). Furthermore, a monocomponent pertussis vaccine containing chemically toxoided PT showed efficacy in a human clinical trial (ref. 12).

Defined whooping cough vaccines have been produced by the isolation of antigens from cultures of B. pertussis. Of the antigens present in acellular vaccines, only PT is toxic. Detoxification of PT has been performed by non-specific chemical modification with formaldehyde, glutaraldehyde, hydrogen peroxide, tetranitromethane and ethyleneimine. Treatment of PT with formaldehyde results in a reduction in immunogenicity and the loss of important protective epitopes, and hydrogen peroxide and tetranitromethane detoxification processes have been shown to significantly reduce the immunogenicity of the molecule. Furthermore, prolonged treatment with glutaraldehyde results in whole-cell pertussis vaccines with low potency. Of further concern is the reversion of formalin-inactivated PT toxoids to toxicity. However, PT can be irreversibly detoxified with appropriate concentrations of glutaraldehyde (ref. 13). Such problems of reduced immunogenicity and residual toxicity have been addressed by genetically manipulating the tox operon to produce inactivated PT analogs (refs. 14,15).

The tox operon has been cloned and sequenced from several strains of B. pertussis, and consists of a single promoter and a polycistronic arrangement of the subunit genes in the order S1, S2, S4, S5 and S3. To remove the enzymatic activity of S1, functional amino acids within the subunit were proposed on the basis of biochemical studies or sequence comparisons with other bacterial toxins and subjected to in vitro mutagenesis. Truncated S1 proteins were produced in Escherichia coli and used to demonstrate that the amino terminus of S1 is required for enzymatic activity. An important region was located between Tyr-8 and Pro-14 with an amino acid sequence similar to sequences in cholera toxin (CT) and E. coli heat-labile toxin (LT) (refs. 16,17). Amino acids in this region that contribute to the ADP-ribosyltransferase activity of PT were identified by substitution mutagenesis. In particular, the Arg-9 to Lys-9 replacement was found to greatly reduce enzymatic activity (ref. 18). A second region of S1, located between Val-51 and Tyr-59, is also conserved in CT and LT. This region was also mutated and some of the residues were shown to be involved in the toxicity of PT, including Ser-52 and Arg-58 (refs. 15,19). The glutamic acid residue at position 129 in the S1 subunit was identified as a residue involved in catalysis or NAD binding (ref. 20), and substitution at this site resulted in a substantial reduction in enzymatic and toxic activities. PT has also been detoxified by mutating Trp-26, His-35 and Cys-41 (ref. 15).

Pertussis toxin has also been detoxified by modification of its cell binding properties, for example by deletion of Asn-105 in the S2 subunit and Lys-105 in the S3 subunit, and by substitution of the Tyr-82 residue in S3 (refs. 21,22). However, the characteristics of the carbohydrate binding sites are imperfectly understood, and a definitive application of this approach has not yet been achieved. Since the molecular mechanism by which PT exerts its various biological activities are still not completely understood, other methods for identifying functional amino acid residues are also useful.

One such method of the present invention is based upon examination of the three-dimensional (3D) structure of PT. A useful embodiment of this approach is to relate previously determined features of the functional sites of PT to the observed structural geometry in order to provide greater insight into the underlying molecular mechanisms. This permits the rational mutation of PT at preselected sites to maximize (for example) detoxification but retain immunogenicity. In particular, it allows for modifying PT at sites differently involved in the biological activity of PT. Another embodiment of this approach is to compare the 3D structure of PT with those of other bacterial toxins with some functional and/or structural resemblance to PT. These include diphtheria toxin (DT) (ref. 23), Pseudomonas exotoxin A (ETA) (refs. 24,25), the heat-labile toxin of E. coli (LT) (refs. 27,28) and verotoxin-1 (VT) (ref. 29).

A particularly useful application of the crystallographic method is to examine the 3D structure of crystalline complexes of PT with molecules relevant to its biological activity. In this way, the amino acid residues of PT responsible for interaction with such ligands can be determined by direct inspection, allowing rational strategies to be developed for their replacement or modification in order to alter the biological activities of PT.

Suitable examples of such molecules are carbohydrates representing the natural ligands for PT found as components of cell-surface glycoconjugates. Some of the characteristics of PT-binding glycosyl chains have been determined by direct binding studies of PT or PT subunits to glycoproteins, glycolipids and cell surfaces (refs. 6,7,8), or by competitive inhibition of the binding or biological activity of PT by small oligosaccharides (refs. 6,7,30). Examples of oligosaccharides that might be expected as a result of such work to form defined complexes with PT are shown in Table 1 below (The Tables appear at the end of the disclosure). Once the amino acids responsible for interaction with these ligands have been identified, they may be modified (for example, by mutagenesis) to enhance or diminish this interaction and thereby alter the biological activities of PT.

Other examples of functionally relevant PT binding molecules are effectors, such as ATP, and substrates, such as NAD, transducin or other G-protein. Since synthetic peptides representing the C-terminal 20 amino acids of the α-subunits of transducin and other G-proteins have been shown to be substrates for the ADP-ribosyltransferase activity of PT, these molecules are also candidates for the generation of crystalline complexes with PT. In so far as NAD itself can be hydrolysed by PT, it may be preferable to seek a non-hydrolysable or poorly hydrolysed analog of NAD for the purpose of forming a stable complex amenable to X-ray crystallography. Alternatively, the study can be performed using a PT analog with inherently low catalytic activity, such as that in which the Glu-129 residue of S1 has been replaced by Gly (ref. 15). Moreover, since ligands are expected to bind to defined regions of the protein surface, it may not be necessary to employ the holotoxin in every case. For example, information on the binding sites of NAD or transducin may be obtained by examining the crystal structure of complexes with the isolated S1 subunit.

SUMMARY AND GENERAL DESCRIPTION OF INVENTION

In accordance with one aspect of the present invention, there is provided a method of predicting at least one site contributing to the biological activity of pertussis holotoxin, which comprises analyzing a three-dimensional structure of crystalline pertussis holotoxin determined by X-ray crystallography in relation to known information concerning protein structure and function to identify the at least one site.

Such a biological activity of pertussis holotoxin may include toxicity, cell-binding, mitogenicity, enzymatic activity and adjuvanticity of the pertussis holotoxin. The at least one site which is predicted by the method provided herein may comprise a single amino acid or a sequence of amino acids.

Such analyzing step may comprise comparing the three-dimensional structure of pertussis holotoxin with known three-dimensional structures of enzymes with substantial functional resemblance to pertussis holotoxin (including bacterial toxins having ADP-ribosyl transferase activity), and identifying structurally conserved regions between the pertussis holotoxin and the enzymes.

Such analyzing step also may comprise comparing the three-dimensional structure of pertussis holotoxin with known three-dimensional structures of other proteins with carbohydrate binding properties, and identifying regions of structural resemblance of the pertussis holotoxin to the proteins.

In these procedures, analysis may also be effected by aligning amino acid sequences of pertussis holotoxin with those of the enzymes or proteins with carbohydrate binding properties, as the case may be, according to structural equivalence (i.e., the structurally conserved regions or regions of structural resemblance, respectively) determined by the identification step.

The analyzing step further may comprise locating, within the three-dimensional structure of pertussis holotoxin, amino acid residues known to contribute to the biological activity of the holotoxin, and identifying spatially-proximate amino acid residues interacting with said known amino acid residues within said three-dimensional structure.

Following identification of the at least one site by the procedure provided herein, the identified at least one site may be modified to alter the biological activity of the pertussis holotoxin, which modification may be effected by genetic, chemical or biochemical means.

Accordingly, the present invention includes the use of the three-dimensional structure of crystalline pertussis holotoxin determined by X-ray crystallography for identifying at least one site in the pertussis holotoxin molecule contributing to the biological activity, including any of the activities noted above.

In accordance with a further aspect of the present invention, there is provided a method of identifying at least one site in pertussis holotoxin that interacts with a molecule that is capable of forming a complex with the holotoxin, the method comprising:

(a) providing a crystalline complex between at least a portion of pertussis holotoxin and the molecule;

(b) determining the three-dimensional structure of the complex by X-ray crystallography; and (c) analysing the structure to identify the at least one interacting site.

The at least one identified site may contribute to toxicity, cell binding, mitogenicity, enzymatic activity or adjuvanticity of the pertussis holotoxin.

The at least a portion of the holotoxin with which the complex is formed may be the entire pertussis holotoxin, an analog thereof, a subunit of the holotoxin, a portion of a subunit, or a combination of subunits.

The step of forming the complex between the molecule capable of forming a complex with the holotoxin and the at least a-portion of the holotoxin may comprise exposing crystals of the at least a portion of the holotoxin under conditions to effect formation of the crystalline complex without substantial disruption of the crystals.

The molecule capable of forming a complex with the holotoxin may be a ligand, such as a cell-surface ligand, including carbohydrates, such as a glycolipid or a glycoprotein, an effector molecule, such as an adenine nucleotide, including ATP, or a substrate for the enzymatic activity of PT. Such substrates include NAD and analogs of NAD that are not substantially hydrolysable by pertussis toxin. The substrate may also be a GTP-binding protein (a G-protein), an α-subunit of a GTP-binding protein or a C-terminal fragment of an α-subunit of a GTP-binding protein. Convenient GTP-binding proteins include $G_i$, $G_o$ and transducin.

Following identification of the at least one site by the procedure provided herein, the identified at least one site may be modified, for example, by genetic, biochemical, or chemical means, to alter a biological activity, such as toxicity, enzymatic activity, mitogenicity cell-binding and adjuvanticity, of the pertussis holotoxin.

The at least one identified site may be at least one amino acid and may be modified by effecting mutagenesis of a tox operon encoding the holotoxin to remove or replace a nucleotide sequence coding for said at least one amino acid residue and to produce a mutant tox operon, and expressing the mutant tox operon in a Bordetella organism to produce the modified holotoxin.

The present invention further comprises a crystalline form of isolated pertussis holotoxin in which the molecules of pertussis toxin have the three-dimensional structure represented by FIGS. 1 and 2 described below. The crystalline form of pertussis holotoxin may be in dimeric form, as shown in FIG. 8, described below. The crystalline form of pertussis holotoxin may have a space group $P2_12_12_1$ with cell dimensions a=163.8 Å, b=98.2 Å and c=194.5 Å. The crystalline form of pertussis holotoxin may be in the form of a complex with a molecule capable of forming a complex with the holotoxin, as described in detail above. Specific examples of such complexes may have the three-dimensional structure represented by FIGS. 10 and 11, described below, or by FIGS. 13 and 14, described below.

In addition, the present invention includes a crystalline form of isolated pertussis holotoxin characterized by atomic co-ordinates specified in accession no. 1 PRT of the Brookhaven Protein Data Bank, Brookhaven, N.Y. USA.

The provision of a crystalline form of pertussis holotoxin allows a comparison with other proteins having functional resemblance to pertussis holotixin (for example bacterial toxins from *Campylobacter jejuni* and *Clostridium botulinum*) with an aim to beneficially modifying such other proteins. For example, bacterial toxins are frequently protective immunogens but require detoxification before they can be used as immunogenic compositions. The ability to identify currently unknown sites that contribute to toxicity of such toxins by a comparison with the three dimensional structure of pertussis holotoxin provides a technique for detoxification of such toxins to provide useful immunogenic but non-toxic analogues.

The crystalline form of pertussis holotoxin as provided herein is of a particularly high purity and is useful as a primary standard for measuring the quantity, purity or efficacy of less pure compositions containing PT.

The present invention further includes a method for the production of a modified pertussis holotoxin, which comprises (a) identifying at least one amino acid residue of the holotoxin for modification by utilizing the prediction procedure provided herein; (b) effecting mutagenesis of a tox operon encoding the holotoxin to remove or replace a nucleotide sequence coding for the at least one amino acid residue and to produce a mutant tox operon; and (c) expressing the mutant tox operon in a Bordetella organism to produce the modified holotoxin.

In an additional aspect of the invention, there is provided a method for producing a modified form of at least a portion of pertussis holotoxin, comprising (a) forming a crystalline complex between at least a portion of pertussis holotoxin and a molecule capable of complexing with the holotoxin; (b) determining a three-dimensional structure of the complex; (c) analysing the structure to identify at least one amino acid residue of the at least a portion of pertussis holotoxin interacting with the molecule; (d) effecting mutagenesis of a nucleotide sequence encoding the at least a portion of the pertussis holotoxin to remove or replace a codon for the at least one amino acid and/or to insert at least one codon adjacent the codon for the at least one amino acid to produce a mutant nucleotide sequence; and (e) expressing the mutant nucleotide sequence to produce the modified form of at least a portion of pertussis holotoxin. The at least a portion of pertussis holotoxin may be pertussis holotoxin or an analog thereof and the step of expressing the mutant nucleotide sequence is effected in a Bordetella organism. Alternatively, the at least a portion of pertussis holotoxin may be a subunit of the holotoxin, a portion of such a subunit or a combination of subunits. The at least one additional codon may be inserted adjacent the 3'-codon of the nucleotide sequence encoding the S1 subunit, in particular a codon coding for a negatively-charged amino acid, for example, Asp or Glu.

The identified amino acid residue in these procedures for producing modified products may comprise at least one amino acid residue which contributes to a biological activity, which may comprise toxicity, cell-binding, mitogenicity, enzymatic activity and adjuvanticity.

The at least one amino acid residue which is mutated may comprise one of those residues as specified in Table 3 below and the substitution made also may be as set forth in Table 3. The at least one amino acid residue also may be located from residue 184 to 203 or from residue 211 to 220 of subunit S1 of the holotoxin.

The invention additionally includes a mutant pertussis holotoxin wherein at least one amino acid residue in the S1, S2, S3, S4 or S5 subunits is substituted by another amino acid residue or deleted, provided by the procedure described herein. The at least one amino acid residue which is modified in this aspect of the invention is listed in Table 3 below. Specific amino acid residue substitutions in the S1, S2, S3, S4 and S5 subunits also are described in Table 3 below.

Particular embodiments of the invention include PT analogs having mutations S2 Lys-83→Ala, S2 Arg-125→Ala and S3 Arg-125→Ala. The activities of such analogs are shown in Table 6 below.

The mutant pertussis holotoxin may comprise modification of at least one amino acid residue located from 184 to 203 or located from 211 to 220 of subunit S1 of the holotoxin. The modification in residues 184 to 203 may be effected to render the same more hydrophilic while the modification in residues 211 to 220 may be effected to eliminate recognition by proteolytic enzymes.

The mutant pertussis holotoxin provided herein may further comprise at least one additional amino acid provided at the C-terminal end of the S1 subunit, particularly a negatively-charged amino acid, particularly Asp or Glu.

The present invention also extends to nucleic acid molecules encoding the PT analogs as provided herein.

BRIEF DESCRIPTION OF DRAWINGS

The file of this patent application contains at least one drawing executed in color, namely FIG. 1, 2, 6, 10, 11 and 13. Copies of this patent with color drawing(s) will be provided by the Patent and Trademark Office upon request and payment of the necessary fee.

FIG. 4 shows a sequence alignment of structurally equivalent residues in the active sites of four ADP-ribosylating toxins, namely PT, LT, ETA and DT (SEQ ID NOS: 1 to 20);

FIG. 5 shows a sequence alignment of the different PT B-subunits (S4, S5 and the C-terminal parts of S2 and S3 (respectively SEQ ID NOS: 24, 25, 22 and 23)) and the B-subunits of LT and VT (respectively SEQ ID NOS: 21 and 26);

FIG. 7 shows a sequence alignment of 47 structurally equivalent residues in MBP (SEQ ID NOS: 39 to 44) and the N-terminal domains of S2 and S3 (respectively SEQ ID NOS: 27 to 32 and 33 to 38);

EXAMPLES

Figure 1:
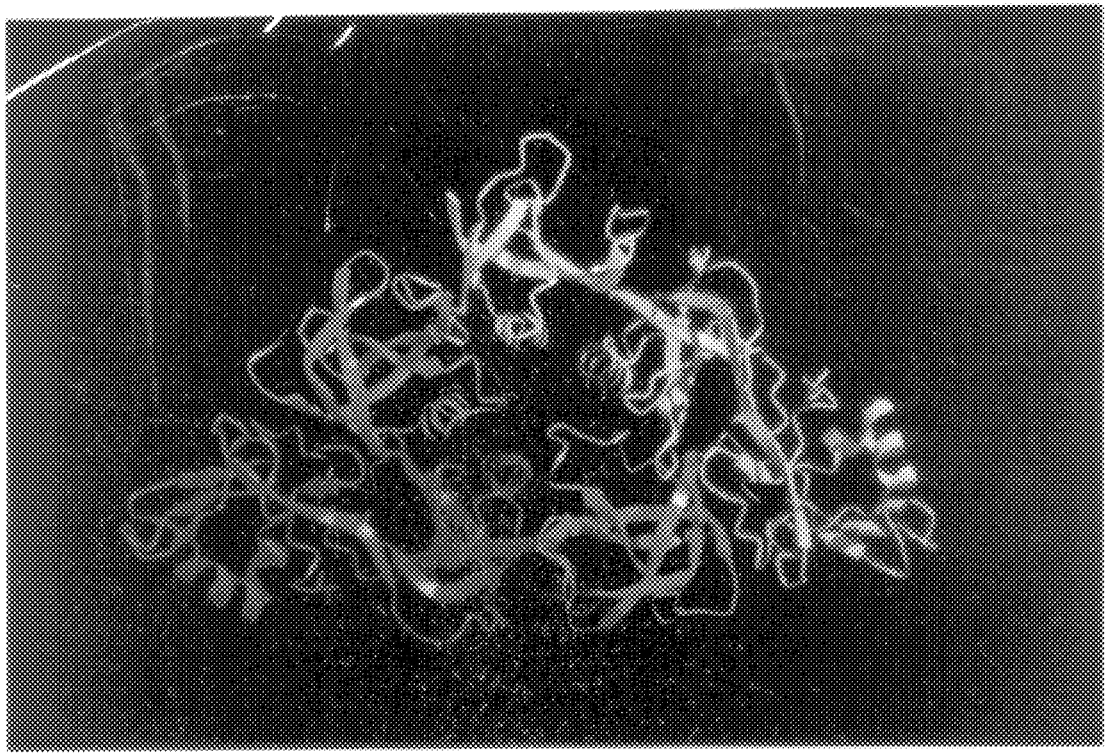
FIG. 1 shows a schematic representation of the B-oligomer of pertussis toxin viewed along the pseudo-5-fold axis from the side opposite to S1. Subunit S2 is shown in pale blue, S3 in dark blue, S4 in red, and S5 in yellow.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example describes the crystallization of pertussis toxin (PT), data collection and phase determination.

PT was purified from culture supernatants of *B. pertussis* strain 10536 (ref. 8), and crystallized in space group $P2_12_12_1$ with cell dimensions a=163.8 Å, b=98.2 Å, c=194.5 Å, by a modification of conditions described by Spangler et al. (ref. 32). PT crystals have also been reported by Raghavan et al. (ref. 33). According to the modified conditions, stock solutions of PT in 0.1M K-phosphate, pH 8.0, 50% v/v glycerol were stored at −20° C., and samples (1.2 to 2.0 mg/ml) were dialysed against buffer 1 (25 mM Na/K-phosphate, 0.25M KCl, 0.02% $NaN_3$, pH 8.0). Seed crystals were grown by the hanging drop method, equilibrated against a precipitant of 0.3 to 0.5M KCl in buffer 1. Macroseeds were transferred to protein drops equilibrated against 0.26 to 0.35M KCl in buffer 1 and typically grew to a size of 0.3 mm×0.2 mm×0.15 mm. Diffraction data were collected at room temperature using a synchrotron radiation source (λ=1.04 Å) and image plate detector on the Weissenberg camera (ref. 34). The data were processed using WEIS (ref. 35) and programs in the CCP4 package (obtained from Daresbury Laboratory, Daresbury, Warrington WA4 4AD, England). The x-ray diffraction data obtained is summarized in Table 2 below, and now described in detail.

"Native" data: Initially, the best data set (native 1) was collected to 3.3 Å resolution from a crystal soaked in 20 mM trimethyl lead acetate for 14 days, although these data do not differ significantly from true native data. Later, a 2.9 Å data set (native 2) was collected that merged poorly with native 1 and the derivative data. The native 2 data were collected from a crystal that had been soaked in 30 mM NAD for 3 days, although difference Fourier analyses show no evidence of NAD binding.

Heavy atom derivatives: True native crystals were soaked respectively in saturated d-μ-iodobis-(ethylenediamine) diplatinum(II) nitrate (PIP) for 7 days, saturated $(NH_3)_2Pt(NO_2)_2$ for 7 days, 1 mM $KIrCl_6$ for 3 days, 1 mM $KAu(CN)_2$ for 5 days, 1 mM $OsCl_3$ for 3 days.

Multiple isomorphous replacement (MIR) phase determination: Seven heavy atom sites were identified in the PIP derivative with SHELXS (ref. 36) using native 1 as native data. Parameters for these sites were refined with MLPHARE (ref. 37), and further sites in the PIP and other derivatives were found by iterative use of difference Fourier analyses and heavy atom refinement. The overall figure of merit was 0.44 (25–3.5 Å).

Density modification: The MIR phases were improved by solvent flattening with the DEMON density modification package (obtained from Dr. F.M.D. Vellieux, IBS/LCCP, 41 Ave. des Martyrs, 38027 Grenoble, Cedex 1, France), using a conservative solvent fraction of 50%. The resulting map showed a clear solvent boundary outlining two holotoxin molecules in the asymmetric unit. The relative orientation of the two molecules was determined by a domain rotation function (ref. 38), using structure factors calculated in space group P1 from spheres of density corresponding to each molecule. The translation needed to superimpose rotated density from one molecule onto the density sphere for the second molecule was calculated with a phased translation function (ref. 38,39). An envelope around the two toxin molecules was calculated from a local correlation map (ref. 40), enclosing 44% of the asymmetric unit. Two-fold averaging and solvent flattening were carried out using the DEMON package, with gradual phase extension from 5.0 to 3.5 Å.

The atomic co-ordinates of the crystalline pertussis holotoxin as determined herein have been deposited as Accession Number 1 PRT of the Brookhaven Protein Data Bank, Brookhaven, N.Y., USA.

Example 2

This Example describes model building of the pertussis toxin molecule.

Interpretation of the electron density map of PT was facilitated by the recognition of similarity with known toxin structures, which helped to define the secondary structure connections and chain direction in a large part of the map. A molecular model of the A1-subunit of LT was positioned in the density corresponding to S1 using a domain rotation function and phased translation function. In this way, the N-terminal three-quarters of S1 was shown to resemble the A1-subunit of LT. Five separate VT B-monomers were placed in the central part of the B-oligomer density using the program O (ref. 41). The central part of the B-oligomer was shown to share the fold common to VT and LT. The peripheral domains of the B-oligomer (formed by the N-terminal portions of S2 and S3) were built without reference to a known structure. A partial model of one PT molecule was built using O, based on a skeletonised map and guided by the positioned models. The structure of the second PT molecule of the asymmetric unit was generated using the non-crystallographic symmetry operation. Subunits S2 and S3 were easily distinguished by differences in side-chain electron density, especially at positions 26 (Lys/Gly), 50 (Arg/Pro), 65 (Gly/Gln), 143 (Trp/Arg) and 148 (Arg/Ala).

The initial PT model, containing 85% of the residues with 5% fitted as alanines, was refined by rigid body refinement and energy minimization using X-PLOR (ref. 42). Phases from the refined model were combined with the original MIR phases using SIGMAA (ref. 43). Errors in the initial PT model were clearly shown in the map calculated with the combined phases. Iterative cycles of model building, simulated annealing refinement with X-PLOR (including a non-crystallographic symmetry restraint), and combination of model and MIR phases resulted in a model that was 98% complete. The 3.3 Å model was then refined against the 2.9 Å data set (native 2) using rigid body refinement and simulated annealing in X-PLOR. Further model building and refinement were carried out with the higher resolution data.

Figure 2:
FIG. 2 shows a schematic representation of pertussis toxin viewed perpendicular to the 5-fold axis of the B-oligomer. Subunit S1 is shown in green, and the other subunits as in FIG. 1.

This PT model contains 1868 amino acid residues (934 in each molecule, comprising 224/235 in S1, 196/199 in S2 and S3, 110/110 in both copies of S4, 98/99 in S5) with no solvent molecules. The electron density is compatible with the amino acid sequence from *B. pertussis* strain 10536 (ref. 44). Missing residues are in regions of poor density at the N-termini of S1 (one residue), S2 (three residues), S3 (three residues) and S5 (one residue), and ten residues (211–220) near the C-terminus of S1. Schematic representations of the B-oligomer and the holotoxin are shown in FIGS. 1 and 2.

The model includes restrained individual isotropic temperature factors. It has a crystallographic R-factor of 19.5% for all reflections between 10.0 and 2.9 Å and tightly restrained geometry. The rms deviation from ideality is 0.014 Å for bond distances and 1.8° for bond angles. In the Ramachandran plot of each molecule, 82% of the residues are in the most favoured regions and none are in disallowed regions (refs. 45). The rms difference in coordinates of all main chain atoms after superposition of the two molecules is 0.21 Å.

Example 3

This Example shows the analysis of the structure of pertussis toxin.

The overall structure of the PT molecule, which contains six separate polypeptide chains, is shown schematically in FIGS. 1 and 2, which emphasize the considerable topological complexity of PT. They depict the B-oligomer viewed along the 5-fold axis from the side opposite to S1 and the holotoxin viewed perpendicular to the 5-fold axis of the B-oligomer. In these and other figures, $\alpha$-helices are shown as spirals, $\beta$-strands as thick arrows and less-regular segments of the polypeptide chains as thin filaments. Most details of the individual amino acid residues have been omitted for simplicity.

The structure of PT displays some striking similarities with other bacterial toxins, but also some significant differences which have important implications for the functional activity of PT. FIG. 1 shows the planar triangular arrangement of the B-oligomer. The polypeptide chain folds of S4, S5 and the C-terminal domains of S2 and S3 are remarkably similar to each other and to the corresponding subunits of VT and LT. The presence of a central pore with approximate 5-fold symmetry is also characteristic of VT and LT. The N-terminal domains of subunits S2 and S3, which constitute the acute apices of the triangular arrangement, are unique to PT and therefore of particular significance in understanding the interactions between PT and receptor molecules on target cells. FIG. 2 demonstrates that S1 sits on top of the planar arrangement of the B-oligomer along its 5-fold central axis.

The two copies of S4 have essentially identical folds, and can be superimposed with an rms difference for all 110 C$\alpha$ atoms of 0.56Å (0.32Å after omitting 21 C$\alpha$ atoms in loops and at the C-terminus). Superposition of S2 and S3 shows a significant shift only at the C-terminus, with an rms difference for the remaining 188 C$\alpha$ atom pairs (residues 4–91) of 0.63Å. Secondary structure was assigned with DSSP (ref. 46). S1; $\beta1$:6–11, $\alpha1$:15–21, $\beta2$:23–24, $\alpha2$:32–37, $\beta3$:50–54, $\alpha3$:57–77, $\beta4$:83–92, $\beta5$:97–99, $\alpha4$:100–111, $\alpha5$:118–127, $\beta6$:129–133, $\beta7$:135–136, $\beta8$:141–150, $\beta9$:155–162, $\beta10$:191–193, $\beta11$:198–199, $\alpha6$:200–205, $\beta12$:225–227, $\alpha7$:228–231. S2 and S3

N-terminal domains; β1:27–29 α1:32–37, α2:39–48, β2:54–56, β3:61–63, β4:70–72, β5:84–93. S2 and S3 C-terminal domains, β6:100–105, β7:106–113, β8:119–125, β9:128–135, α3:146–159, β10:163–173, β11:183–191. S4; β1:6–10, β2:11–20, β3:27–36, β4:48–55, α1:63–74, β5:78–89, β6:92–102. S5; β1:5–9, β2:10–20, β3:23–31, β4:37–43, α1:51–66, β5:70–74, β6:84–91.

Subunit S1

The N-terminal 175 residues of S1 of PT show structural homology with the enzymatic portion of the A-subunit of LT, consistent with their similar catalytic functions. All secondary structure elements within this region are conserved, except for helix α5 in PT which has no equivalent in LT. Strands β4 and β8, and helices α3 and α4 of PT are longer than in LT, and there are significant differences in connecting loops. The disulphide bond in S1 (Cys-41/Cys-201) is not structurally equivalent to the disulphide bond of LT, but in both cases reduction is essential for catalytic activity. Residues 176–235 of Si have no structural homology in LT. Analysis of C-terminal deletion mutants has shown that this part of S1 is not essential for catalytic activity in vitro (refs. 47,48). A stretch of residues in extended conformation is followed by two short strands (β10 and β11), a helix (α6), and a further strand (β12). β-strands 10–12 form a small anti-parallel sheet. The C-terminus enters a "pore" in the centre of the B-oligomer with a short helix (α7) and ends within a pore.

The amount of surface buried between S1 and B-oligomer is much larger than between the A and B portions of LT. However, the interface in PT is typical of that found in stable oligomeric proteins (ref. 49). Thus, the numbers of hydrophobic, hydrogen-bond and electrostatic interactions are not unusual for protein interfaces of this size. The interaction between the C-terminus of S1 (228 to 235) and the B-oligomer pore accounts for 28% of the buried surface. Residues 211–220 of S1 (between α6 and β12) have poor density and could not be modelled. A disordered region occurs in a roughly equivalent part of the LT A-subunit, at the junction of A1 and A2, and proteolytic cleavage in this region is necessary for membrane translocation. Tryptic cleavage of S1 at Arg-218 has been found to enhance activation of PT in vitro (ref. 50).

Active site

The structure of the active site of S1 is depicted in FIG. 3. A number of amino acid residues previously found to be implicated in the active site of S1 are included in this figure and labelled R9 (Arg-9), R13 (Arg-13), W26 (Trp-26), H35 (His-35), C41 (Cys-41), S52 (Ser-52), E129 (Glu-129) and C201 (Cys-201).

As expected, the active site of S1 is structurally homologous to the active sites of LT, ETA and DT. FIG. 4 shows a sequence alignment of structurally equivalent residues in the active sites of these four toxins. Identical residues are high-lighted in bold lettering; only two residues, corresponding to Tyr-8 and Glu-129 in PT, are conserved in all four toxins. These glutamate residues have also been shown to be essential for enzymatic activity in each of the toxins. In PT, the side chain of Glu-129 is within hydrogen bonding distance of His-35, Ser-52 and Gln-127. Mutation of His-35 or Ser-52 is also associated with considerably reduced ADP-ribosyltransferase activity (refs. 19,64). Reduction of the disulphide bridge between Cys-41 and Cys-201 of S1 that is required for expression of enzymatic activity may induce a conformational change permitting productive binding of NAD.

B-oligomer

The C-terminal half of S2 and S3, both copies of S4, and S5 have similar folds, consisting of six antiparallel β-strands forming a closed β-barrel, capped by an α-helix between the fourth and fifth strands (FIG. 1). This fold has been recognized previously in several proteins which bind either an oligosaccharide or an oligonucleotide, and named the "OB fold" (ref. 51). Other proteins containing the OB fold include the B-subunits of LT and VT-1. A sequence alignment based upon a structural superposition of the B-subunits of PT, LT and verotoxin-1 is shown in FIG. 5 and demonstrates that there is no detectable sequence homology. Adjacent B-subunits associate mainly through antiparallel β-sheet interactions to form a rather asymmetrical pentamer around a central pore lined by five helices. The same type of B-subunit interaction, but with more perfect 5-fold symmetry, is seen in the B-pentamers of LT and verotoxin-1. In PT, the most extensive interactions between B-subunit monomers are those of S2 with S4 and S3 with S4, in agreement with the observation that the B-oligomer dissociates in 5M urea into an S2/S4 dimer, an S3/S4 dimer and an S5 monomer (ref. 52). The N-terminal half of S2 and S3 form separate domains at the periphery of the B-oligomer. Each of these domains consists of five β-strands and two α-helices, with a fold similar to that of the lectin domain from a rat mannose binding protein (MBP) (53) (FIG. 6), which belongs to a family of calcium dependent (C-type) eukaryotic lectins.

Receptor-binding sites

Most of the sequence differences between S2 and S3 are found near the N-termini, suggesting that these regions may contain determinants of carbohydrate binding specificity. The crystal structure shows that, although the N-terminal domains of S2 and S3 show overall structural homology with a member of the family of C-type eukaryotic lectins (FIG. 6), they apparently lack its functional region. Thirty-two conserved amino acids in the sequences of known C-type lectins are believed to contribute to the carbohydrate recognition domain (CaRD). Features of the N-terminal sequences of S2 and S3 thought to be characteristic of the CaRD motif were reported (ref. 8), but with the exception of the disulphide bond (Cys-23/Cys-87), they are not consistent with the observed structural relationship. None of the remaining CaRD residues can be identified in the structure-based sequence alignment of S2 and S3 with MBP (FIG. 7). In the MBP structure, the calcium ligands lie within a long loop between strands β2 and β3 that was found to be the carbohydrate binding site (ref. 54). This loop has no structural equivalent in S2/S3 (FIG. 6), and there is no evidence that calcium is required for receptor binding of PT.

Evaluation of experimental findings in the light of the crystal structure points to two regions of the N-terminal domains of S2 and S3 that may be involved in receptor binding. Both sites are exposed and lie on the probable membrane binding surface of the toxin (furthest from S1). The first site is the loop between residues 18 and 23. This sequence in S2 was found to be homologous to residues 62 to 67 in wheat germ agglutinin (ref. 55), which form part of the sialic acid binding site determined crystallographically (ref. 56). Synthetic peptides incorporating this sequence bind to sialic acid-containing glycoconjugates (ref. 55). These segments of the two crystal structures are in fact very similar; residues 18 to 23 of S2 can be superimposed on residues 62 to 67 of wheat germ agglutinin with an rms difference of only 1.03 Å for 22 main chain atoms. A second site that may have a role in carbohydrate recognition is helix α2 (residues 39 to 48). Exchange mutation of residues 37 to 52 between S2 and S3 was reported to be associated with an exchange of binding specificities (ref. 8).

The central pentameric domain of the PT B-oligomer may also be involved in receptor binding, as in the previously recognized proteins that contain the OB fold. Crystallographically determined binding sites of other proteins with this fold (ref. 51) are in variable loops between β2–β3, β4-α and β5–β6 (VT-1 numbering), but they lie in similar locations with respect to the overall structure. An extended binding site on S2 or S3 might span one or more of these C-terminal domain loops (β7–β8, β9-α3 and β10–β11), as well as parts of the N-terminal domain. Mutations in the vicinity of β5–β6 and β10–β11 of S2 and S3 have been found to affect receptor binding (refs. 21,22).

Figure 8:
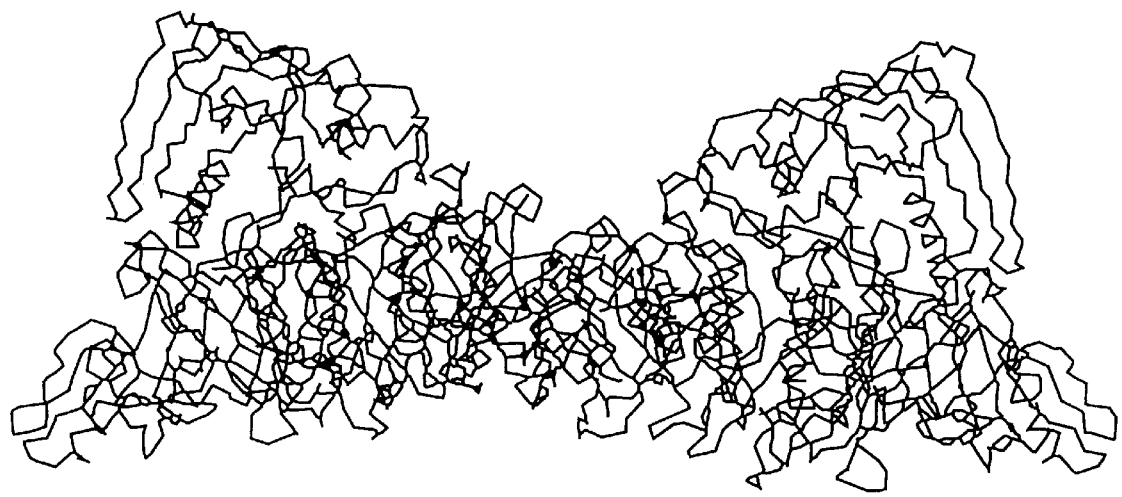
FIG. 8 shows a Cα tracing of the dimeric form of PT existing in the crystal.

Another feature of the PT crystal structure relevant to cell surface binding activity is the observation that PT crystallizes as holotoxin dimers. Association is mediated by edge-on interaction between pairs of S2 and S4 subunits on each molecule, such that the two 5-fold axes are almost parallel and the two cell-binding B-oligomer faces almost coplanar. This arrangement is illustrated in FIG. 8, in which the polypeptide chains are represented as line segments joining amino acid Cα atoms. The area of surface buried at the interface is sufficient for stable complex formation in solution, suggesting that dimeric PT presenting an extended multivalent cell-binding region is important under physiological conditions.

Example 4

This Example describes the identification of functional amino acid residues in pertussis toxin by examination of its 3D structure.

Figure 3:
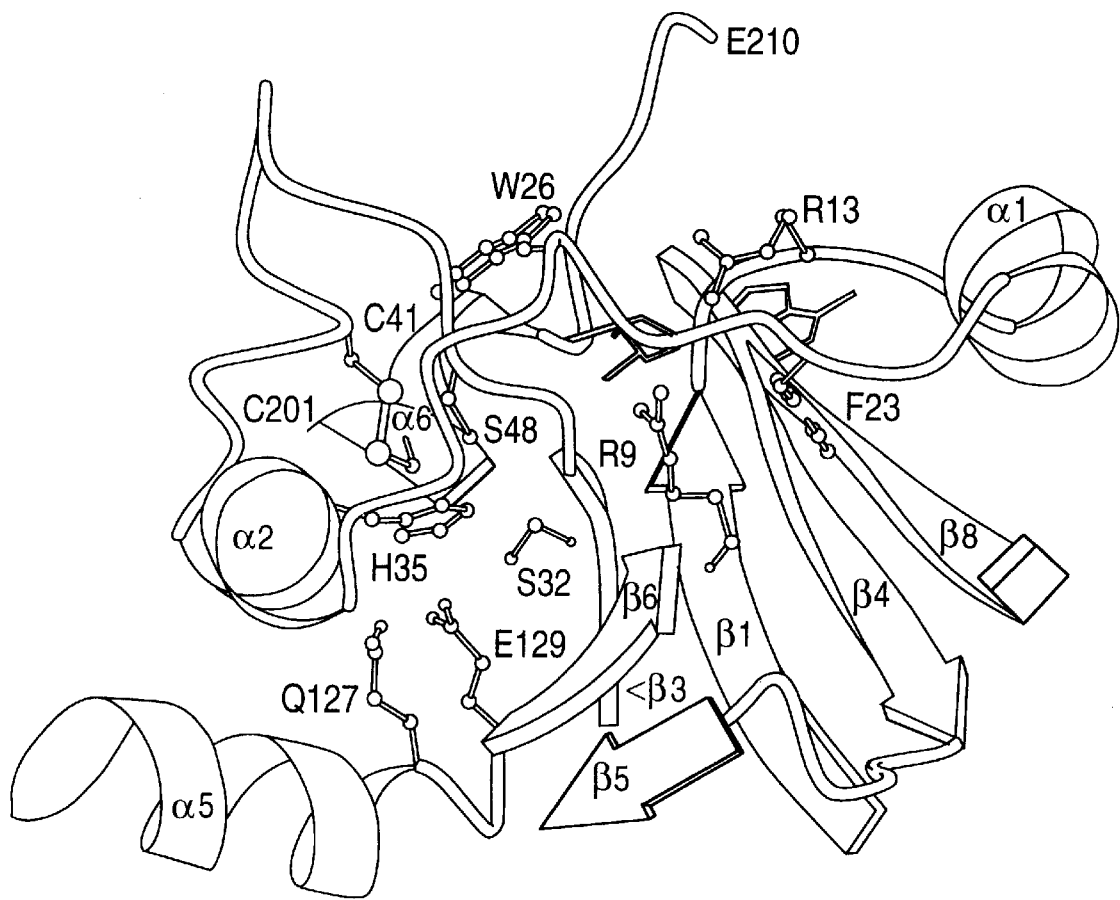
FIG. 3 shows a schematic representation of the active site of subunit S1 of pertussis toxin with individual amino acid residues identified according to the standard one-letter coding system.

Inspection of the crystal structure of PT in comparison with those of LT, ETA and DT has permitted a molecular model of the active site of S1 to be constructed (FIG. 3). This model accounts for the functional importance of a number of amino acid residues previously implicated in the active site of S1 by the methods outlined above. It further provides direction for the identification of additional previously unrecognized residues whose modification might be expected to yield PT analogs with altered biological activity. Thus, in one embodiment of the present invention, there are provided amino acid residues in subunit S1 of PT contributing to catalytic activity or binding of substrates or effectors, which include nicotine adenine dinucleotide (NAD).

A model for NAD binding to S1 was generated by superimposing the active site of PT onto DT in crystals of DT bound to a dinucleotide adenylyl-3', 5'-uridine monophosphate (ref. 23). The position of the adenine moiety of this molecule, denoted by 'Ad' in FIG. 3, may represent the position of the adenine moiety of NAD bound to S1. Most of the amino acid residues already implicated in the catalytic activity of S1 are clustered in a region adjacent to this site and are labelled in FIG. 3. They include R9 (Arg-9), R13 (Arg-13), W26 (Trp-26), H35 (His-35), C41 (Cys-41), S52 (Ser-52), E129 (Glu-129) and C201 (Cys-201).

Also marked in FIG. 3 are several other amino acid residues located in spatially proximate relation to the previously identified amino acid residues or with the predicted position of bound NAD, and therefore also likely to be important to the enzymatic activity of S1. These amino acid residues are F23 (Phe-23), S48 (Ser-48), V51 (Val-51), Q127 (Gln-127), L131 (Leu-131), G199 (Gly-199) and A200 (Ala-200). Analogues of PT in which one or more of these amino acid residues are deleted, replaced or modified are therefore predicted to exhibit altered biological activity.

A second approach to modifying PT is to interfere with its ability to bind to target cells. Another embodiment of this invention therefore relates to the provision of amino acid residues in the B subunits of PT involved in or influencing binding to cell surface glycoconjugate receptors.

Figure 6:
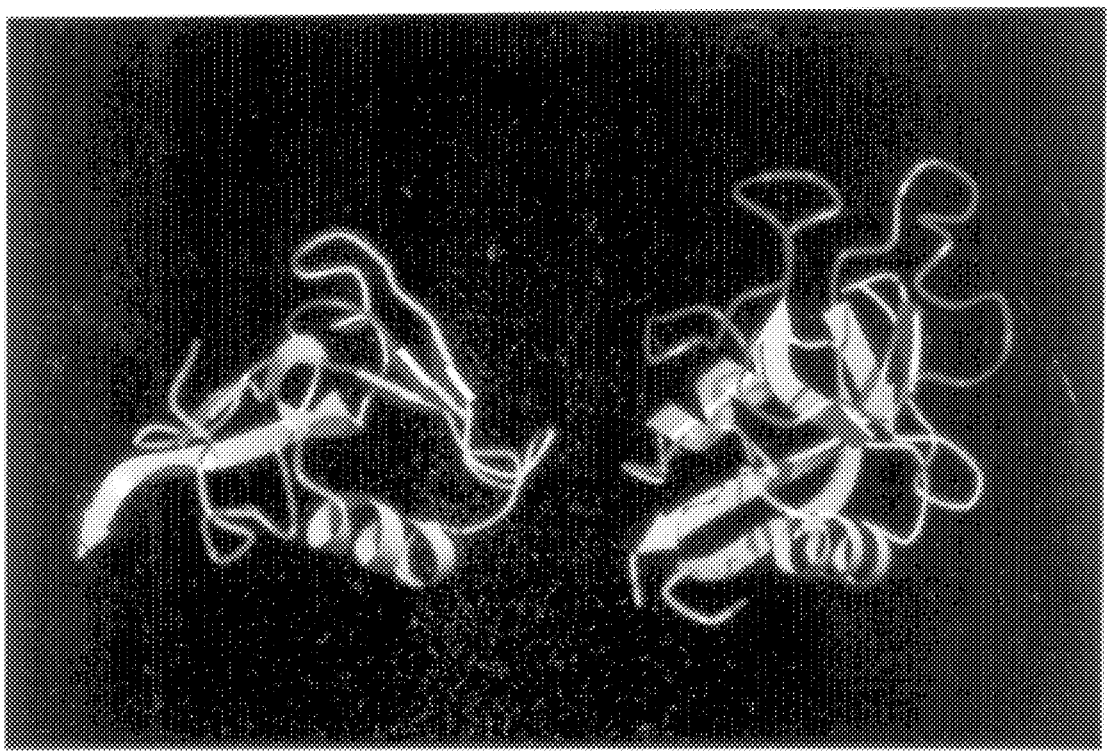
FIG. 6 shows a schematic representation of the N-terminal 93 residues of S3 (left) and rat mannose binding protein (MBP) (right)

The crystal structure points to the significance of an α-helical region between residues 38 and 50 of subunits S2 and S3 in attachment of PT to glycoconjugate receptors. This region, seen at the base of the representation in FIG. 6, is also conserved in MBP according to structure, and to some extent also according to sequence (FIG. 7). These S2 and S3 helices are also partially exposed and could contribute to a cell-binding surface. It has been reported that sequence changes in this region of S2, or exchange of sequences between S2 and S3, affect the carbohydrate binding specificity of isolated S2 and S3 subunits (ref. 8). Examination of the crystal structure of PT shows that this helix forms one face of a groove across the surface of S2 and S3 into which the most functionally sensitive amino acid residues are directed. The opposite face of this groove is occupied by amino acid residues His-15, Gln-16, Leu-82 and Lys-83 in S2, and by residues Gln-15, Gln-16, Tyr-82 and Arg-83 in S3. Replacement of Tyr-82 of S3 has already been shown to diminish the biological activity of PT (ref. 22), but the significance of the other sites to glycoconjugate binding of PT has not previously been recognized. Analogues of PT in which one or more of these amino acid residues are deleted, replaced or modified are therefore predicted to exhibit altered biological activity.

Dimerization of PT might also be expected to affect its ability to bind to target cells. Although dimerization occurs between pairs of S2 and S4 subunits on two adjacent PT molecules, similar dimerization between pairs of S3 and S4 subunits is stereochemically possible but does not occur, indicating that S2 contains unique amino acid determinants promoting dimerization. A comparison between S2 residues at the dimer interface and the corresponding S3 residues is as follows:

Residue No. 20 52 54 63 66 67 81 82 83
Subunit S2 Tyr Trp Ile Leu Glu Tyr Asp Leu Lys
Subunit S3 Tyr Trp Ile Leu Ala Tyr Ile Tyr Arg The S2 residues Glu-66, Asp-81, Leu-82 and Lys-83 not conserved in S3 are therefore predicted to be responsible for dimerization of PT. Thus analogues of PT in which one or more of these amino acid residues are deleted, replaced or modified are expected to exhibit altered biological activity. As described above, amino acid residues 82 and 83 were also implicated in glycoconjugate binding on other grounds.

Detailed examination of the crystal structure of PT reveals that significant interactions between S2 and S4 subunits on adjacent molecules also involve residue Trp-52 of S2 and residues Asp-1, Tyr-4, Thr-88 and Pro-93 of S4. Analogues of PT in which one or more of these amino acid residues are deleted, replaced or modified are therefore also predicted to exhibit altered biological activity.

A third approach to detoxification of PT is to impede the ability of the catalytic S1 subunit to dissociate from the B-oligomer, which is important in the context of in vitro enzymatic activity, and is believed also to be important in vivo. A further embodiment of this invention therefore relates to the identification of amino acid residues of subunit S1 likely to influence the ability of a functional moiety of S1 to disengage from the remainder of the molecule.

A significant feature of subunit S1 as it appears in the crystal structure is the lack of electron density associated with amino acid residues 211–220, indicating that this portion of the polypeptide chain is disordered and unlikely to be essential for polypeptide chain folding or stabilization. The amino acid sequence corresponding to this region is as follows:

Residue No. 211 215 220
Sequence Ala Met Ala Ala Trp Ser Glu Arg Ala Gly (SEQ ID NO: 45).

However, the downstream C-terminal sequence 228 to 235 is observed to be important in establishing contact between S1 and the central pore of the B-oligomer alluded to previously. A similar situation exists in the crystal structure of LT, where a disordered region occurs in a structurally analogous part of the catalytic LT-A subunit just upstream of the C-terminal segment which interacts strongly with the LT-B pore. Significantly, proteolytic cleavage in this disordered region is necessary for activation of LT. It has not been previously suggested that proteolytic cleavage of S1 is required for activation of PT; however, the S1 segment 211 to 220 contains recognition sites for trypsin (Arg-217) and chymotrypsin (Met-212 and Trp-215), and is readily cleaved by these enzymes in vitro (ref. 50). Moreover, a truncated form of S1 lacking all amino acid residues beyond position 180 is known to exhibit almost full NAD-glycohydrolase activity in vitro in the absence of B-oligomer (ref. 57), indicating that the C-terminal region is not essential once S1 is disconnected from the rest of the PT molecule. Deletion or truncation of the loop between S1 residues 211 and 220, or substitution of key amino acid residues within this loop, may therefore yield PT analogs with altered biological activity.

Upstream of the region of disordered structure in S1 is a hydrophobic region extending from residues 184 to 203, which has the characteristics predicted for a membrane-spanning segment (ref. 58). The amino acid sequence corresponding to this region is as follows:

| Residue No. | 184 | | | | 190 | | | |
|---|---|---|---|---|---|---|---|---|
| Sequence | Val | Ala | Ser | Ile | Val | Gly | Thr | Leu | Val | Arg |
| Residue No. | 195 | | | | 200 | | 203 | |
| Sequence | Met | Ala | Pro | Val | Ile | Gly | Ala | Cys | Met | Ala |
| (SEQ ID NO: 46) | | | | | | | | |

Reduction of the disulfide bond between Cys-41 and Cys-201, together with proteolytic cleavage of the C-terminus as described above, are therefore predicted to expose a region of S1 suited to anchoring a functional moiety of S1 in a cellular membrane. This functionality is predicted to facilitate translocation of S1 and its diffusion along an intracellular membrane. Introduction of polar amino acid residues within this region may therefore yield PT analogues with altered biological activity.

Example 5

This Example describes the generation of a crystalline complex between PT and a biantennary undecasaccharide derived from human serum transferrin, and determination of its 3D structure. The composition of this carbohydrate, obtained from BioCarb Chemicals, is as follows:

Neu5Ac(2α,6)-Gal(1β,4)-GlcNAc(1β,2)-Man(1α,6)
                                                              |
                                            Man(1β,4)-GlcNAc(1β,4)-GlcNac
                                                              |
Neu5Ac(2α,6)-Gal(1β,4)-GlcNAc(1β,2)-Man(1α,3)

PT was purified and crystallized as described in Example 1. Native crystals were soaked in a 10 mM solution of the carbohydrate in 25 mM Na/K-phosphate, 0.3M KCl, 0.02% NaN$_3$, pH 8.0 for 5 h, or until the surface became etched, then removed for mounting. Crystals dissolved when soaked in a 30 mM solution of the carbohydrate. Data were collected from a single crystal using a synchrotron radiation source and image plate detector on the Weissenberg camera (ref. 34). The data were processed using WEIS (ref. 35) and programs in the Daresbury CCP4 package, and were 87% complete between 10 and 3.5 Å, with a merging R-factor of 9.7% (25.1% at 3.5 Å) and multiplicity of 3.4.

Crystals of the PT-sugar complex remained isomorphous with the native PT crystals (space group P2$_1$2$_1$2$_1$, with cell dimensions a=163.8 Å, b=98.2 Å, c=194.5 Å). As before, the asymmetric unit contained two molecules related by non-crystallographic two-fold symmetry. However, the PT-sugar data merged poorly with data from native crystals ($R_{merge}$ on amplitudes 23.5%). The structure was solved by rigid body refinement of the native PT structure against the PT-sugar data using X-PLOR (ref. 42). Initially each toxin molecule in the asymmetric unit was refined independently (two rigid groups), and later the two molecules were divided into their six individual subunits (12 rigid groups). The starting R-factor was 36.5% (10-8 Å), and fell to 22.0% (10-4 Å) at the end of rigid-body refinement. The resulting model showed an overall rotation of 1.2° relative to the original native PT structure, but there were no significant internal domain shifts.

A difference electron density map was calculated using the new model phases with SIGMAA-weighted Fourier coefficients (ref. 43). The three highest peaks per asymmetric unit on the map (7.0–8.4 times the rms electron density) corresponded to three sugar moieties, which were modelled using the program O (ref. 41). Although bound carbohydrate was observed at equivalent sites on subunits S2 and S3, only three of the four possible binding sites in the asymmetric unit were occupied. The fourth potential site, on the S2 subunit of molecule 2, was evidently not accessible to this carbohydrate owing to a packing interaction with a symmetry-related PT molecule. Crystals dissolved when soaked in 30 mM carbohydrate, perhaps because this interaction was disrupted.

Figure 9:
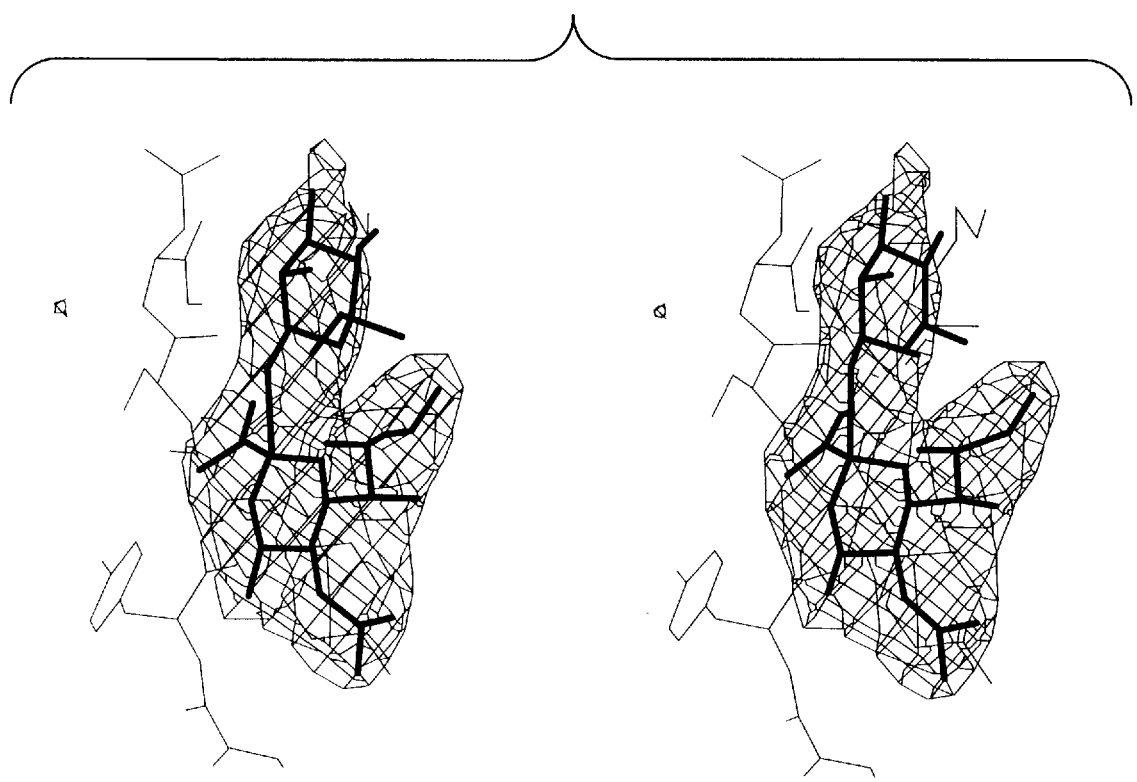
FIG. 9 is a stereo view showing the difference electron density for a biantennary undecasaccharide from human serum transferrin bound to subunit S3 of PT.

At each occupied binding site, clear electron density was present for only two carbohydrate residues, the other nine remaining disordered. The chemical identities of the ordered residues were assigned by assessing the fit of every possible pair of neighbouring residues in the transferrin undecasaccharide to the electron density of a difference Fourier map. Structure factors and phases for this map were calculated using the model after rigid body refinement (Example 5), and before any attempt had been made to build the carbohydrate. Part of this map is shown in FIG. 9. Although the resolution of the diffraction data is only 3.5 Å, the result was unambiguous: only the terminal NeuAc(2α, 6)-Gal moiety could fit the observed electron density. The linkages between all other adjacent pairs of sugar residues were such that both residues could not be placed in density at the same time.

Two additional amino acid residues at the N-terminus of S2 of PT molecule 2 were added to the native PT model, and the complete structure was refined by simulated annealing with X-PLOR, using an additional empirical energy function for carbohydrate (ref. 59). The conformation of the bound NeuAc (2α, 6)-Gal group was found to be almost identical at each binding site, and close to one of the low energy conformations for this molecule determined using energy calculations and NMR spectroscopy (ref. 60).

The current PT/sugar model contains 1870 amino acid residues (934 in molecule 1 and 936 in molecule 2), six carbohydrate residues, and no solvent. Atomic temperature factors are those of the native PT model, except for unique atoms (including the carbohydrate) which have fixed B-factors of 20 Å². The crystallographic R-factor is 18.3% for all reflections between 10.0 and 3.5 Å. The rms deviation from ideality is 0.015 Å for bond distances and 1.9° for bond angles. The rms difference in coordinates of all main chain atoms after superposition of the two molecules is 0.18 Å.

Example 6

This Example describes the analysis of the structure of the complex between pertussis toxin and the undecasaccharide from human serum transferrin, and the identification of functional amino acid residues in pertussis toxin.

Figure 10:
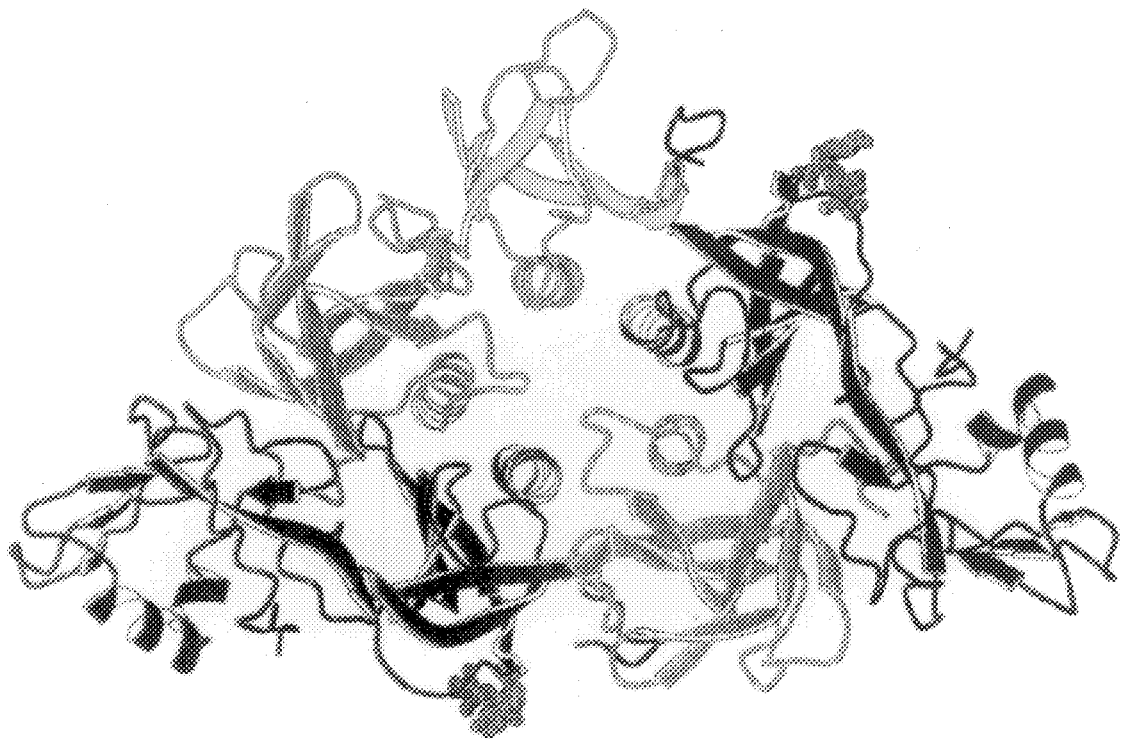
FIG. 10 shows a schematic representation of the complex between PT and a biantennary undecasaccharide from human serum transferrin in the same orientation as FIG. 1. Subunit S2 is shown in pale blue, S3 in dark blue, S4 in red, S5 in yellow and the carbohydrate in mauve.
Figure 11:
FIG. 11 shows a schematic representation of the complex between PT and a biantennary undecasaccharide from human serum transferrin in the same orientation as FIG. 2. Subunit S1 is shown in green, and the other subunits and the carbohydrate as in FIG. 10.
Figure 12:
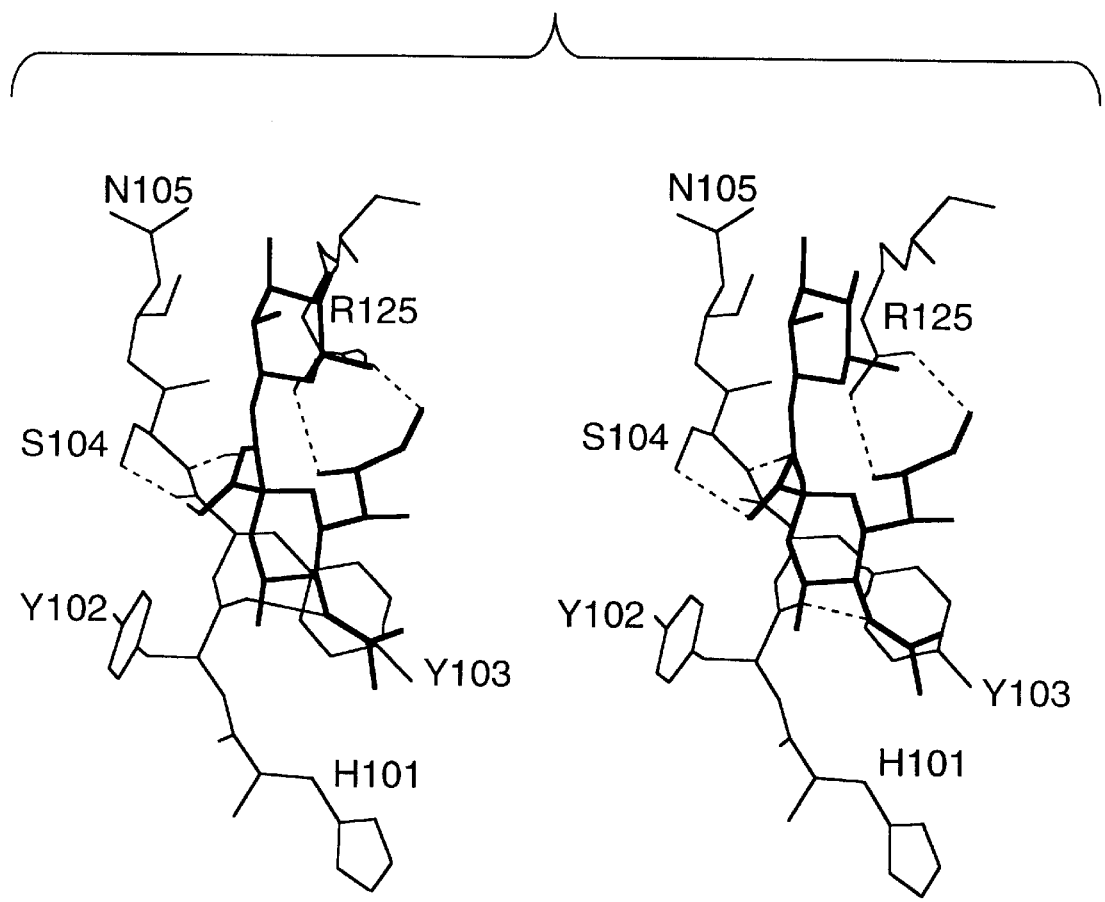
FIG. 12 is a stereo view showing the binding to PT subunit S2 of the terminal NeuAc(2α, 6)Gal moiety of a biantennary undecasaccharide from human serum transferrin. This Figure depicts the sugar in relation to the Cα trace of S2 and details of the binding site, with dashed lines indicating hydrogen bonds between the sugar (thick lines) and protein (thin lines)

The binding sites of the disaccharide moieties on S2 and S3 in relation to the complete structure of PT are shown in FIGS. 10 and 11. The shortest distance between binding sites in the asymmetric unit is ~65 Å, which excludes the possibility of bivalent interaction of a single sugar molecule through its two equivalent arms. Interactions between the carbohydrate and the protein are virtually identical at each of the three binding sites in the asymmetric unit. The galactose makes no interactions with the protein, but the sialic acid is within hydrogen bonding distance of polar or charged groups on Tyr-102, Ser-104 and Arg-125, as detailed in Table 4 below and depicted in FIG. 12. In addition, the sialic acid ring makes hydrophobic contacts with the aromatic rings of Tyr-102 and Tyr-103. All amino acid residues that interact directly with the sialic acid are fully conserved between S2 and S3.

The present finding of three sialic acid binding sites per asymmetric unit agrees with a recent report (ref. 61) describing an isomorphous derivative of the same PT crystal form. In that case, native PT crystals were soaked in a mercuric derivative of sialic acid, resulting in three mercury sites, as identified by difference Patterson techniques. The positions of peaks in the published Harker sections are consistent with the mercury atoms lying within 1 to 2 Å of the position of C6 of galactose in the undecasaccharide complex. This suggests that the binding mode for sialic acid is very similar in the two cases.

The transferrin undecasaccharide used in this study was chosen because its composition and linear structure are typical of the oligosaccharide chains of glycoproteins, such as fetuin, known to bind strongly to PT, and of the surface glycoproteins of mammalian cells, such as Chinese hamster ovary cells, that are susceptible to intoxication by PT. Furthermore, the crystallographic results described herein are consistent with the findings that asialofetuin has severely reduced affinity for PT (ref. 6), while a variant CHO cell line lacking terminal sialic acid residues does not bind PT and is not susceptible to its action (ref. 7). These observations indicate that the terminal sialic acid residues of glycosyl chains are important for the physiologically significant binding of PT to mammalian cells, and suggest that the binding site on PT disclosed by the present invention has physiological significance.

The observed sugar interaction site lies in the C-terminal portion of S2/S3, which has the oligomer-binding fold (ref. 51) also present in the cell-binding B-subunits of members of the cholera toxin and Shiga toxin families. This portion of the structure is thus expected to contribute to binding to cell surface receptors, although additional sites are also likely to exist in the N-terminal domains of S2 and S3, as discussed above. The S2 and S3 residues observed to interact with the sugar are indeed consistent with some experimental studies of receptor binding. There is good evidence that tyrosines are involved; firstly, it has been found that the toxin is inactivated by iodination (which typically affects tyrosines), but can be protected by binding to fetuin-agarose (ref. 62); secondly, recombinant forms of PT with mutations or deletions involving Tyr-102 and Tyr-103 of S2 or S3 show reduced biological activities (refs. 21,22). Cell-binding activity is also attenuated by deletion of Asn-105 in S2 or Lys-105 in S3 (refs. 21,22), residues that are in close proximity to those observed in the crystal structure to interact direct with the sugar. However, the central importance of residues Ser-104 and Arg-125 of S2 and S3 in binding sialic acid residues has not been previously recognized. Analogues of PT in which one or more of these amino acid residues are deleted, replaced or modified are therefore predicted to exhibit altered biological activity.

Example 7

This Example describes the generation of a crystalline complex between PT and ATP, and determination of its 3D structure.

PT was purified and crystallized as described in Example 1. Native crystals were soaked in a 30 mM solution of ATP in 25 mM Na/K-phosphate, 0.3M KCl, 0.02% $NaN_3$, pH 8.0 for 1.5 day. Data were collected from a single crystal using a synchrotron radiation source and image plate detector on the Weissenberg camera (ref. 34). The data were processed using WEIS (ref. 35) and programs from the BIOMOL package (obtained from the laboratory of Chemical Physics, University of Groningen, Nijenborgha 16, 9747 AG, Groningen, Holland), and were 57% complete to 2.5 Å, with a merging R-factor of 9.3% (33.1% at 2.5 Å) and a multiplicity of 3.0. Owing to radiation damage during data collection, the maximum resolution of the diffraction decreased from 2.5 Å for the first images to 3.3 Å for the last. Therefore data completeness beyond 3.3 Å dropped rather quickly to 18% for the highest resolution shell. At 3.3 Å the data were 88% complete, with a merging R-factor of 7.60 (17.5% at 3.3 Å) and a multiplicity of 3.3.

Crystals of the PT-ATP complex remained isomorphous with the native PT crystals (space group $P2_12_12_1$, with cell dimensions a=163.8 Å, b=98.2 Å, c=194.5 Å). As previously, the asymmetric unit contained two holotoxin molecules related by non-crystallographic two-fold symmetry, and the data merged reasonably well with the native data ($P_{merge}$ on amplitudes was 15.4% for all reflections in the range 30.0-2.9 Å). The structure was solved by, rigid body refinement of the native PT structure against the PT-ATP data, using X-PLOR (ref. 42). The B-values for all atoms were reset to 25 Å², and all 12 subunits were treated as independent rigid bodies. The starting R-factor was 31.1% (10-3 Å) and fell to 28.4% (10-3 Å).

A difference electron density map was calculated using the new model phases with SIGMAA-weighted Fourier coefficients (ref. 43). In the resulting map, the density for the ATP molecule was clearly recognizable as the most prominent feature of the map. Using the program O (ref. 41), a model of the ATP molecule was inserted into the difference electron density. The density also indicated that the C-terminus of subunit Si and the side chain of Arg-69 of one of the S4 subunits, denoted S4b, changed their conformation. To obtain an unbiased density for these atoms, the C-terminal residues 234 and 235 of subunit S1 were removed and Arg-69 of S4b was modified to an alanine residue. Positional refinement of this model, with a restraint to keep the two non-crystallographically related holotoxin molecules in the asymmetric unit similar, decreased the R-factor from 29.2% (8.0-2.7 Å) to 25.5% (8.0-2.7 Å). In a new difference map, calculated as described above using the phases of the new model, there was clear electron density for the two C-terminal residues of subunit S1 and the Arg-69 side chain, which were reintroduced into the model.

Repeated cycles of model building and X-PLOR refinement finally resulted in a model for the complex in which each member of the dimer contained 935 amino acid residues (7259 atoms) and 31 atoms from the bound ATP molecule. In addition 81 water molecules were added per asymmetric unit. The R-factor for this model was 22.9% (8.0-2.7 Å), with tightly restrained B-values (rms difference between bonded atoms 1.3 Å$^2$) and protein geometry (rms deviations from ideal bond lengths and angles 0.017 Å and 2.0° respectively).

Example 8

This Example describes the analysis of the structure of the complex between pertussis toxin and ATP, and the identification of functionally important amino acid residues in pertussis toxin.

Figure 13:
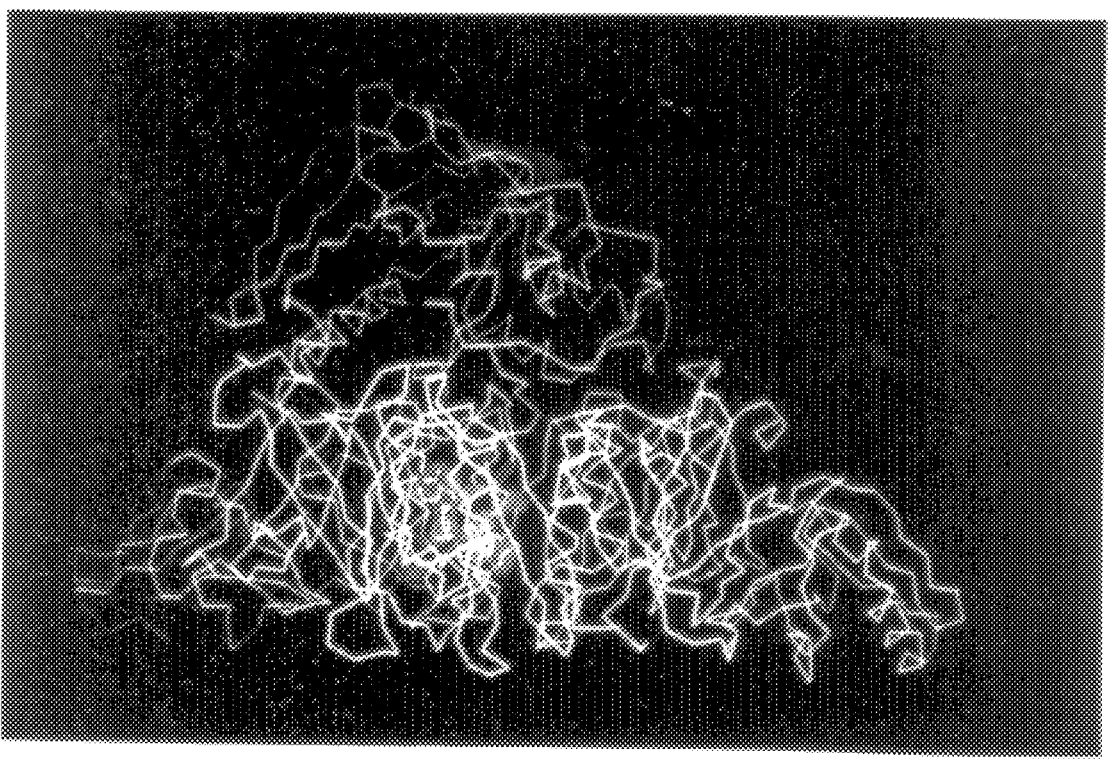
FIG. 13 is a schematic representation of the complex between PT and ATP, demonstrating the electron density difference between the complex and the holotoxin alone. This electron density difference, shown in light blue, is largely attributed to the bound ATP molecule. Subunit S1 is shown in green and the B-oligomer in violet.
Figure 14:
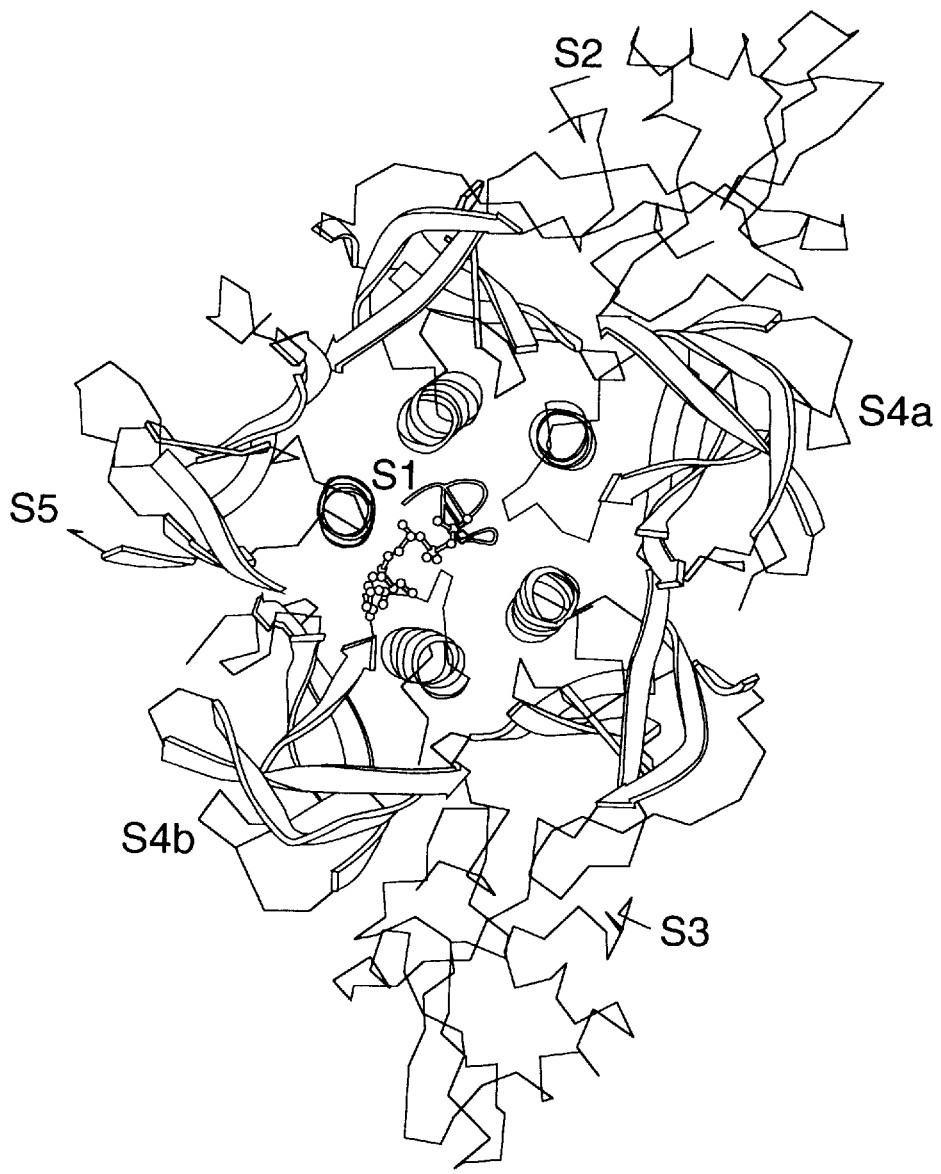
FIG. 14 shows a schematic representation of the complex between PT and ATP, viewed approximately along the pseudo-5-fold axis. The helices and strands common to the five B-subunits are depicted as ribbons and arrows respectively. The N-terminal domains of subunits S2 and S3 and the chain fragments connecting the secondary structural elements are depicted as lines. The C-terminus of subunit S1 (residues 226–235) and the ATP molecule are located at the center of the figure and are drawn as a smooth coil and as a ball-and-stick model, respectively. All subunits are labeled on their N-termini.
Figure 15:
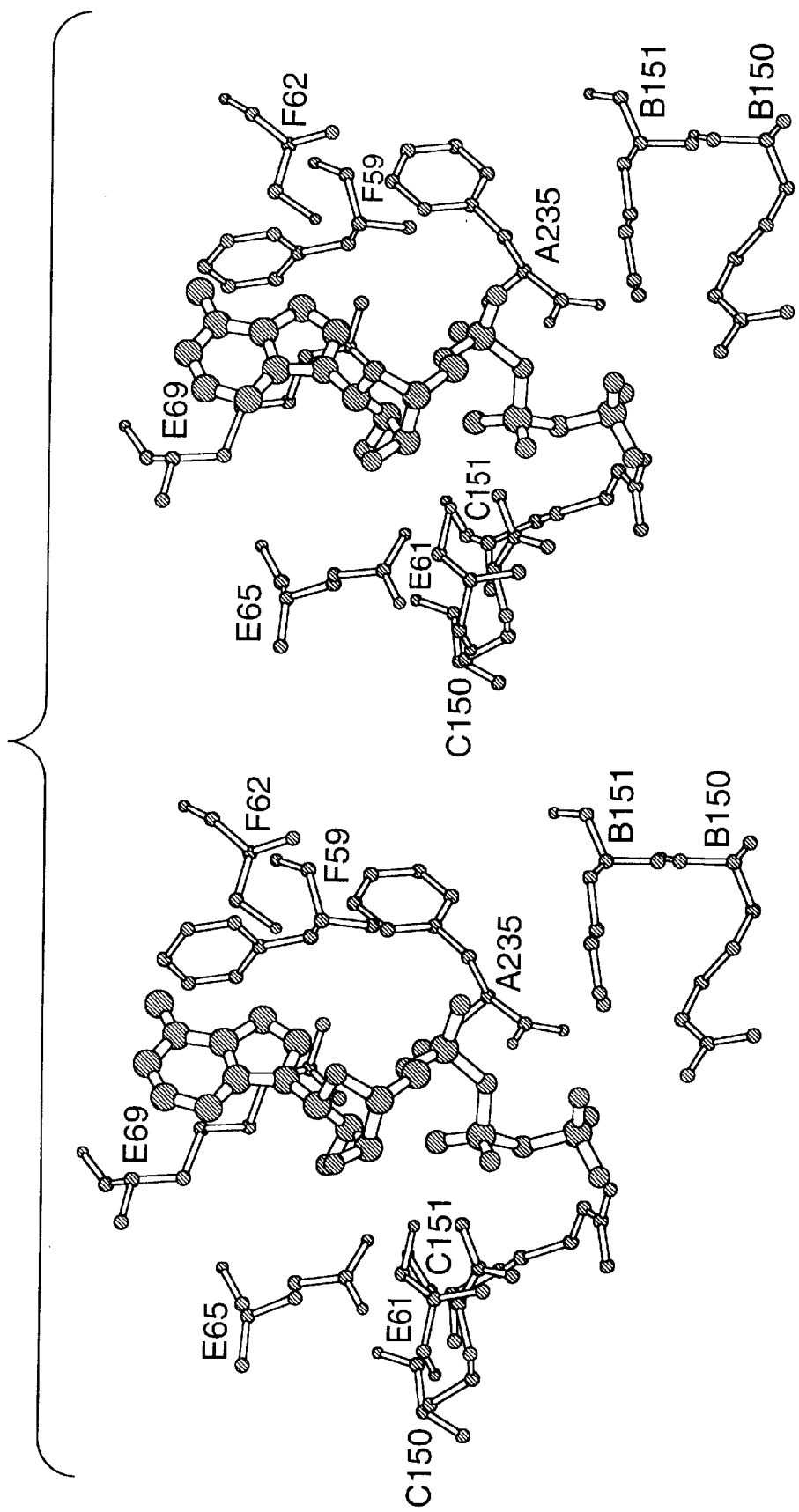
FIG. 15 is a stereo diagram of the ATP binding site, showing the most important residues that interact with the ATP molecule. The residue labels comprise the residue number preceded by a character to indicate in which subunit the residue resides (A, B, C, D, E and F denote S1, S2, S3, S4a, S4b and S5, respectively)

The binding site of ATP in PT molecule 1 is shown in FIGS. 13 to 15. FIGS. 13 and 14 demonstrate that the ATP molecule is located in the central pore created by the pentameric B-oligomer, very close to the C-terminus of subunit S1. FIG. 15 illustrates amino acid residues that significantly interact with the ATP molecule. For simplicity, the individual subunits S1, S2, S3, S4a, S4b and S5 are denoted A, B, C, D, E and F, respectively. The ATP binding site in molecule 2 is almost identical. A list of all protein atoms within 3.5 Å of at least one ATP atom in molecule 1 is given in Table 5 below.

The binding of ATP to the holotoxin does not cause global changes in the quaternary or tertiary structure. The most prominent changes are displacements of the C-terminal three residues of the S1 subunit and the side-chain atoms of Arg-69 of subunit S4b, which are required in order to accommodate the ATP molecule. In addition, movement of the S1 tail helps to reduce the unfavourable electrostatic interactions between the negatively charged phosphate groups of ATP and the negative C-terminal carboxylate group of S1, while movement of Arg-69 enhances the favourable electrostatic interactions between the phosphates and the positive side chain.

Binding of ATP

The triphosphate moiety of the ATP molecule is surrounded by a remarkable number of positively charged amino acid side chains. Thus Arg-150 and Lys-151 of S2, Arg-150 and Arg-151 of S3, and Arg-69 of S4b are all within 3.2 Å of at least one phosphate oxygen. The C-terminal oarboxylate group of subunit S1 is the only protein-derived negative charge within this range of a phosphate oxygen atom. Accordingly, it can be expected that the electrostatic interactions between the three negative charges on the phosphates and the surrounding positive charges of the protein contribute significantly to the overall binding energy of ATP. This conclusion is consistent with studies that show that binding of ADP to pertussis toxin is considerably weaker than that of ATP (refs. 3,4).

The phosphate oxygen atoms O3, O5, O6, O7, O8, O9 and O10 all make hydrogen bonds to at least one protein atom. Important protein residues involved in these hydrogen bonds are the above-mentioned Arg-150 and Lys-151 of S2, Arg-150 and Arg-151 of S3, and Arg-69 of S4b, plus Ser-61 of S4b. Oxygens O2 and O4 appear not to make hydrogen bonds to the protein. The oxygen atoms O2' and O3' of the ribose unit of ATP form hydrogen bonds to Ser-61, Glu-65 and Arg-69 of subunit S4b. Of the four nitrogen atoms in the purine ring of ATP, only N7 takes part in a hydrogen bond, to residue Ser-62 of subunit S5. The other three do not have any contacts within 3.5 Å. However, extensive Van der Waals interactions exist between the purine ring and the alkyl side chain of Arg-69 of S4b. In addition, the phenyl ring of Phe-59 of S5 plays an important role in shaping the cavity for the purine ring, even though its closest distance to the purine ring is 4.4 Å (this residue not listed in Table 5).

Another aspect of the binding of ATP to PT relates to the fact that ATP occupies a site in the central pore of the B-oligomer which would normally be filled with solvent molecules. Most if not all of these solvent molecules would be expected to have some degree of structure, in view of the concentration of charged amino acid residues in the vicinity. Release of these water molecules would increase their entropy, thus giving a favourable contribution to the binding energy of the ATP molecule.

Functional amino acid residues

The functional importance of ATP binding to pertussis toxin lies in its ability to loosen the interaction between the catalytic Si subunit and the B-oligomer, or allow its complete release (refs. 4,67). For example, in the absence of ATP, the in vitro ADP-ribosyltransferase activity of PT is reduced by 20-fold (ref. 67). Modifications to the structure of PT that prevent the release of subunit S1 can thus be expected to substantially affect the biological activity of PT. Accordingly, modifications that prevent ATP binding would also be expected to attenuate the biological activity of PT. Amino acid residues of PT shown to participate in binding ATP according to the forgoing crystallographic analysis are Arg-150 and Lys-151 of subunit S2, Arg-150 and Arg-151 of subunit S3, Ser-61, Glu-65 and Arg-69 of subunit S4b, and Ser-62 of subunit S5. Of these, Arg-69 of subunit S4b is particularly important in view of its involvement in both polar and non-polar interactions with ATP. Ser-61 of subunit S4b and Ser-62 of S5 are significant as being the sole hydrogen bonding partners of O5 and N7 of ATP, respectively, as well as lining the the binding pocket for the ATP molecule. In addition, Gly-58 of S5 occupies a position where any larger amino acid residue would cause steric hindrance of a bound ATP molecule. Analogs of PT in which one or more of these amino acid residues are deleted, replaced or modified are therefore predicted to exhibit altered biological activity.

An alternative approach to hindering the release of S1 required for activation of the toxin is to modify the C-terminus of Si itself, since this segment is pushed aside on binding ATP. Thus extension of the S1 chain by one amino acid would be expected to impede the approach of an ATP molecule. Addition of a negatively-charged amino acid or replacement of the terminal Phe-235 with a negatively charged amino acid residue would provide additional electrostatic repulsion with respect to the triphosphate tail of ATP, while augmenting favourable electrostatic interactions with neigbouring positively charged residues of the B subunits. Such changes would therefore be expected to yield PT analogs with altered biological activity.

Entrance pathway of ATP

To reach its binding site, the ATP molecule must approach the holotoxin from the side of the B-oligomer remote from S1, since no entrance pathway can be found from the opposite side which is blocked by the S1 subunit. Blocking the entrance to this binding site would be expected to prevent activation of the toxin. Amino acid residues flanking the approach to the binding site are Ser-147 of S2, Gly-60 and Ser-61 of subunits S4a and S4b, and Asp-54, Thr-51 and Thr-55 of S5. Modifications to these residues in order to alter their size or polarity, therefore, would be expected to diminish the ability of ATP to bind to PT and hence its ability to activate the holotoxin.

Example 9

This Example describes the production of PT holotoxin analogues containing mutations at the specific sites identified by examination of the crystal structures disclosed herein.

To produce PT analogues containing site-specific mutations, the tox operon may be mutated and the mutant tox operon expressed in recombinant strains of *Bordetella parapertussis* or *Bordetella pertussis*. The extent of detoxification is then estimated by an ADP-ribosyltransferase assay, by the CHO cell clustering assay, and by in vivo assays including histamine sensitisation and lymphocytosis-promotion. The techniques required to produce and analyze these analogues are reported in the following references, each of which is incorporated herein by reference:

U.S. Pat. No. 5,085,862
U.S. Pat. No. 5,221,618
Loosmore, S. et al. (ref. 15)
Zealey, C. et al. (ref. 65)
Zealey, G. et al. (ref. 66)
Loosmore, S. et al. (ref. 22)

Briefly, DNA restriction enzymes were purchased from Bethesda Research Laboratories, Boehringer Mannheim, New England BioLabs, and Pharmacia and used according to the specifications of the manufacturers, All radioisotopes were supplied by New England Nuclear. Standard recombinant DNA techniques were performed as described by Maniatis et al.

The tox operon from the Connaught vaccine strain 10536 and its flanking regions were cloned from a Charon 35 phage library into pUC plasmids. The S1 gene was subcloned into M13mp18 for in vitro site-directed mutagenesis by the phosphorothioate procedure (Amersham). all mutations were confirmed by the dideoxy sequencing method of Sanger et al. Mutated tox operons were cloned into the replicating plasmid pRK404 (ref. 68) and introduced into *B. parapertusis* by conjugation for production of PT analogs.

*B. pertussis* strains were maintained in Bordet-Gengou medium containing 20% fresh defibrinated sheep blood and cultured in Stainer-Scholte medium supplemented with 0.2% (2,6-O-dimethyl)β-cyclodextrin. Culture supernatants were typically harvested after 3 days of growth at 36° C.

Enzyme immunoassays. PT concentration was determined by fetuin capture enzyme-linked immunosorbent assay (ELISA). Nunc Immulon II ELISA plates were coated with fetuin (GIBCO; 2 $\mu$g/ml) for 16 h at 4° C. in 50 mM sodium carbonate, pH 9.6. The plates were then washed three times in phosphate-buffered saline (PBS) containing 0.050% Tween 20. Wild-type PT or sample PT was serially diluted and added to the wells, and the plates were incubated for 30 min at room temperature. After three washes, bound PT was detected with monospecific rabbit anti-PT or anti-S1 antibodies purified by protein A affinity chromatography (Pharmacia) and conjugated to peroxidase. The plates were washed, and tetramethyl benzidine (Allelix Diagnostics Inc.) in 0.005% hydrogen peroxide was added to determine the amount of bound enzyme. The reaction was stopped by the addition of 1M $H_2SO_4$. The $A_{450}$ was determined by using a reference wavelength of 540 nm (Biotek EIA Autoreader model EL310).

Antigenicity immunoassay. A panel of murine monoclonal anti-PT antibodies was developed in our laboratories from splenocytes of mice immunized with detoxified PT. The monoclonal antibody PS21 was shown to recognize the S1 subunit in association with free and fetuin-bound B oligomer. The LP12 monoclonal antibody recognizes the S3/S4 dimer. Polyclonal anti-PT antisera were raised in rabbits immunized with purified PT.

The analogs of PT may have one or more of these amino acid residues deleted, replaced or modified either singly or severally, and either in the absence of or in addition to other mutations. The amino acid residues described herein could be replaced by any other $\alpha$-amino acid, for example, but not exclusively, by means of genetic manipulation in a cellular expression system or by chemical synthesis of individual subunits. It is also understood that certain of these amino acid residues could also be modified subsequent to protein synthesis by chemical or biochemical methods. Such approaches are described in the scientific literature and will be familiar to those skilled in the art.

One consideration in the selection of amino acid residues with which to replace the identified natural amino acid residues is the likely functions of the natural amino acid residues in the toxin, and their spatial and chemical characteristics in relation to the available replacements. This process is facilitated by the exclusive ability of the inventors to inspect the detailed three-dimensional structure of PT outlined in this document, and appraise the unique environment of each amino acid residue.

The present invention, therefore, provides PT analogs in which the amino acid residues specified according to subunit in Table 3 below are deleted, replaced or modified alone or in combination with additional mutations. Preferred amino acid replacements at each site are also shown.

The present invention also provides pertussis toxin analogues in which at least one of the amino acid residues from position 211 to position 220 of subunit S1 is deleted, substituted or modified, either exclusive or inclusive of additional mutations in the PT molecule. Preferably, but not exclusively, one goal of such sequence changes is to remove protease cleavage sites signalled by Met-212, Trp-215 and Arg-217. Examples of preferred amino acid substitutions at these positions are as follows:

Met-211→Ser or Thr
Trp-215→Asn or His
Arg-217→Ser or Gln

The present invention further provides pertussis toxin analogues in which the hydrophobic region between residues 184 and 203 of subunit S1 is rendered more hydrophilic by substitution of one or more non-polar residues by polar or charged residues.

Referring to Table 6, there is shown the characterization of PT analogs having mutations S2 Arg-125→Ala, S3 Arg-125→Ala and S2 Lysine-83→Ala. To determine the concentration of PT analog production, analogs were captured with a polyclonal anti-PT antiserum and detected with a further polyclonal anti-PT antiserum. It is considered that this ELISA gives the most reliable measure of PT analog concentration, since neither capture nor detection depends upon maintenance of any particular single epitope. The ability of PT analogs to bind to fetuin was taken as a measure of the integrity of the fetuin binding sites on S2 and/or S3. Thus, the ratio of the concentration of PT analog determined by the fetuin capture ELISA and the polyclonal capture ELISA (corrected for the ratio of this ratio for wild-type PT) is a measure of the detoxification of the PT analog.

The results shown in Table 6 indicate that PT analogs having amino acid replacements at sites in the S2 and S3 subunits modified by a method comprising (a) identifying at least one amino acid residue of the holotoxin for modification by analyzing a three-dimensional structure of crystalline pertussis holotoxin determined by X-ray crystallography in relation to known information concerning protein structure and function; (b) effecting mutagenesis of a tox operon encoding the holotoxin to remove or replace a nucleotide sequence coding for said at least one amino acid residue and to produce a mutant tox operon; and (c) expressing the mutant tox operon in a Bordetella organism to produce the modified holotoxin, have altered biological activities. In this embodiment the modified biological activity is cell binding.

It is emphasized that the described amino acid replacements only examples of convenient replacements of the identified amino acid residues to disrupt the function of the natural amino acid residues at these locations. Other substitutions, modifications or deletions, according to the methods outlined above, may also be used to achieve modification of pertussis toxin, and are within the scope of the present invention.

SUMMARY OF DISCLOSURE

In summary of this disclosure, the present invention provides the three-dimensional crystal structures of pertussis toxin and of complexes of PT bound to functionally relevant molecules, as determined by X-ray crystallography. These provide the ability to identify functional amino acids for modification to alter the biological properties of PT. Modifications of such amino acids are possible within the scope of this invention.

TABLE 1

Oligosaacharides suitable for forming complexes with pertussis toxin for crystallographic analysis

| Name | Formula |
|---|---|
| lactose | Gal(1β,4)Glc |
| N-acetyllactosamine | Gal(1β,4)GlcNAc |
| 3'-sialyllactose | Neu5Ac(2α,3)Gal(1β,4)Glc |
| 3'-sialyl-N-acetyllactosamine | Neu5Ac(2α,3)Gal(1β,4)GlcNAc |
| 6'-sialyllactose | Neu5Ac(2α,6)Gal(1β,4)Glc |
| 6'-sialyl-N-acetyllactosamine | Neu5Ac(2α,6)Gal(1β,4)GlcNAc |
| lacto-N-biose | Gal(1β,3)GlcNAc |
| 2'-fucosyllactose | Fuc(1α,2)Gal(1β,4)Glc |
| 3'-fucosyllactose | Gal(1β,4)[Fuc(1α,3)Glc] |
| Lewis$^x$ trisaccharide | Gal(1β,4)[Fuc(1α,3)GlcNAc] |
| Lewis$^a$ trisaccharide | Gal(lβ,3)[Fuc(1α,4)GlcNAc] |
| sialyl-Lewis$^x$ | Neu5Ac(2α,3)Gal(1β,4)[Fuc(1α,3)GlcNAc] |
| 1β-2 N-acetylglucosamine-mannose | GlcNAc(1β,2)Man |
| biantennary undecasaccharide | |
| Neu5Ac(2α,6)-Gal(1β,4)-GlcNAc(1β,2)-Man(1α,6) | |
| Man(1β,4)-GlcNAc(1β,4)-GlcNac | |
| Neu5Ac(2α,6)-Gal(1β,4)-GlcNAc(1β,2)-Man(1α,3) | |

TABLE 2

Summary of pertussis toxin X-ray diffraction data.

| | Native 1 | Native 2 | PIP | $(NH_3)_2Pt(NO_2)_2$ | $KIrCl_6$ | $OsCl_3$ | $KAuCN_2$ |
|---|---|---|---|---|---|---|---|
| Number of crystals | 1 | 2 | 1 | 1 | 1 | 1 | 1 |
| Resolution (Å) | 3.3 | 2.9 | 3.4 | 3.4 | 3.6 | 3.4 | 3.4 |
| Unique reflections | 40 277 | 52 740 | 37 389 | 37 200 | 31 494 | 31 389 | 38 182 |
| Completeness (%) | 84 | 75 | 85 | 85 | 85 | 71 | 87 |
| Multiplicity | 3.5 | 6.1 | 3.4 | 3.5 | 3.4 | 2.9 | 3.5 |
| $R_{merge}$ (%)$^a$ | | | | | | | |
| Overall | 8.6 | 9.0 | 10.3 | 10.8 | 10.5 | 10.6 | 8.9 |
| Outer resolution shell | 23.2 | 24.0 | 24.1 | 23.4 | 20.8 | 23.3 | 21.3 |
| $R_{deriv}$ (%)$^b$ | — | — | 15.9 | 15.2 | 24.3 | 20.4 | 11.8 |
| Number of sites | — | — | 16 | 11 | 7 | 7 | 4 |
| Phasing power$^c$ | | | | | | | |
| at 6.0 Å | — | — | 1.71 | 1.33 | 0.96 | 0.88 | 0.46 |
| at 3.5 Å | — | — | 1.19 | 0.88 | 0.79 | 0.62 | 0.26 |

PIP = di-μ-iodobis-(ethylenediamine) di-platinum(II)nitrate.
$^a R_{merge} = \Sigma\Sigma|I_i - <I>|/\Sigma\Sigma I_i$.
$^b R_{deriv} = \Sigma||F_{PH}| - |F_P||/\Sigma F_P|$, where $|F_P|$ comes from native 2 data.
$^c$Phasing power = $[\Sigma|F_H|^2/\Sigma(|F_{PH}(obs)| - |F_{PH}(calc)|)^2]^{1/2}$.

TABLE 3

Functional amino acid residues in pertussis toxin

| Subunit | Residues | Preferred Replacement |
|---|---|---|
| S1 | Phe-23 | Asp or Glu |
| | Ser-48 | Ala |
| | Val-51 | Ile |
| | Gln-127 | Ala or Asp |
| | Leu-131 | Lys or Arg |
| | Gly-199 | Val or Gln |
| | Ala-200 | Ile |
| | Phe-235 | Glu |
| S2 | His-15 | Ala or Thr |
| | Gln-16 | Ala or Thr |
| | Trp-52 | Val |
| | Glu-66 | Ala or Lys |
| | Asp-81 | Ala or Ser |
| | Leu-82 | Ala or Glu |
| | Lys-83 | Glu |
| | Ser-104 | Ala |

TABLE 3-continued

Functional amino acid residues in pertussis toxin

| Subunit | Residues | Preferred Replacement |
|---|---|---|
|  | Arg-125 | Ala |
|  | Ser-147 | Thr |
|  | Arg-150 | Ser |
|  | Lys-151 | Ser |
| S3 | Gln-15 | Ala or Thr |
|  | Gln-16 | Ala or Thr |
|  | Tyr-82 | Ala or Val |
|  | Arg-83 | Glu |
|  | Ser-104 | Ala |
|  | Arg-125 | Ala |
|  | Arg-150 | Ser |
|  | Arg-151 | Ser |
| S4 | Asp-1 | Ala |
|  | Tyr-4 | Ala or Val |
|  | Gly-60 | Val |
|  | Ser-61 | Ala |
|  | Glu-65 | Ala |
|  | Arg-69 | Ala |
|  | Thr-88 | Val |
|  | Pro-93 | Ala |
|  | Asp-54 | Glu |
|  | Thr-51 | Tyr |
|  | Thr-55 | Tyr |
|  | Gly-58 | Val |
| S5 | Ser-62 | Ala |

TABLE 4

Hydrogen bonding distances between the sialic acid moiety of the transferrin undecasaccharide and subunits S2 or S3 of PT at three equivalent binding sites in the PT-carbohydrate complex.

| sialic acid atom | protein atom | Hydrogen-bond distance (Å) at each binding site | | |
|---|---|---|---|---|
| | | S2 of Mol 1 | S3 of Mol 1 | S3 of Mol 2 |
| 601A | OG of Ser-104 | 2.8 | 2.9 | 2.8 |
| O1B | N of Ser-104 | 3.1 | 2.7 | 2.8 |
| O8 | NH2 of Arg-125 | 2.6 | 2.5 | 2.4 |
| O9 | NH1 of Arg-125 | 2.6 | 2.5 | 2.5 |
| N5 | O of Tyr-102 | 3.0 | 2.7 | 2.6 |

TABLE 5

Interaction distances less than 3.5 Å between ATP and the protein in the PT-ATP complex

| Subunit | Residue | Atom | ATP Atom | Distance (Å) |
|---|---|---|---|---|
| S1 | Phe-235 | N | O3 | 3.20 |
|  | Phe-235 | N | O3 | 3.20 |
|  | Phe-235 | C | O10 | 3.41 |
|  | Phe-235 | OT1 | O10 | 3.02 |
|  | Phe-235 | OT2 | P1 | 2.99 |
|  |  |  | O2 | 3.34 |
|  |  |  | O3 | 2.74 |
|  |  |  | O4 | 2.68 |
|  |  |  | O7 | 3.25 |
|  |  |  | P3 | 3.45 |
|  |  |  | O8 | 3.31 |
|  |  |  | O10 | 3.11 |
| S2 | Arg-150 | NH2 | O10 | 3.12 |
|  | Lys-151 | CE | O8 | 3.17 |
|  | Lys-151 | NZ | O8 | 3.01 |
| S3 | Arg-150 | NH2 | O6 | 3.24 |
|  |  |  | O7 | 3.35 |
|  | Arg-151 | NH2 | P3 | 3.04 |
|  |  |  | O9 | 2.80 |
|  |  |  | O10 | 2.43 |
| S4b | Met-18 | CE | O4' | 3.27 |
|  | Ser-61 | OG | O2' | 3.07 |
|  |  |  | P2 | 3.37 |
|  |  |  | O5 | 2.93 |
|  |  |  | O6 | 2.97 |
|  | Glu-65 | CD | O3' | 3.39 |
|  | Glu-65 | OE1 | C3' | 3.07 |
|  |  |  | O3' | 2.50 |
|  | Arg-69 | NE | N7 | 3.34 |
|  | Arg-69 | CZ | N7 | 3.21 |
|  |  |  | C8 | 3.12 |
|  |  |  | O3 | 3.45 |
|  | Arg-69 | NH1 | C8 | 3.28 |
|  |  |  | C2' | 3.48 |
|  |  |  | O2' | 3.33 |
|  |  |  | O3 | 2.85 |
|  |  |  | O6 | 3.25 |
|  | Arg-69 | NH2 | N7 | 3.16 |
|  |  |  | C8 | 3.24 |
|  |  |  | O3 | 3.18 |
| S5 | Gly-58 | CA | O2 | 2.57 |
|  | Gly-58 | C | O2 | 3.40 |
|  | Ser-62 | CG | N7 | 2.80 |

TABLE 6

Characterization of PT analogs

| PT Analog | Concentration of PT analog by ELISA μg/mL | | Mean Residual toxicity (%) |
|---|---|---|---|
|  | Fetuin Capture | Polyclonal antibody capture |  |
| S2 Lys-83→Ala | 0.4 | 1.03 | 86 |
|  | 0.3 | 0.87 |  |
|  | 0.38 | 0.85 |  |
|  | 0.33 | 1.74 |  |
| S2 Arg-125→Ala | 0.1 | 1.16 | 28 |
|  | 0.15 | 0.91 |  |
|  | 0.87 | 8.05 |  |
|  | 0.33 | 3.37 |  |
|  | 0.36 | 3.37 |  |
| S3 Arg-125→Ala | 0.25 | 4.95 | 47 |
|  | 1.20 | 9.50 |  |
|  | 1.00 | 6.90 |  |
|  | 0.82 | 1.74 |  |
|  | 0.82 | 5.77 |  |
| Wild-type | 0.4 | 0.6 | 100 |
|  | 0.75 | 2.54 |  |
|  | 1.10 | 4.48 |  |

REFERENCES

1. Kaslow, H. and Burns, D. (1992), *FASEB J.* 6, 2684–2690.
2. Watkins, P. et al. (1984), *J. Biol. Chem.* 260, 13478–13482.
3. Lim, L. K. et al. (1985), *J. Biol Chem.* 260, 2585–2588
4. Burns, D. and Manclark, C. C. 1986), *J. Biol. Chem.* 261. 4324–4327
5. Moss, J., et al. (1986), *Biochemistry* 25, 2720–2725
6. Armstrong, G., et al. (1988), *J. Biol Chem.* 263, 8677–8684.

7. Witvliet, M., et al. (1989), *Infect. Immun.* 57, 3324–3330.

8. Saukkonen, K., et al (1992), *Proc. Natl Acad. Sci. U.S.A.* 89, 118–122

9. Oda, M, et al. (1984), *J Infect. Dis.* 150, 823–833.

10. Sato, H. and Sato, Y (1984), *Infect. Immun.* 46, 415–421.

11. Halperin, S., et al. (1991), *J Infect. Dis.* 163, 355–361.

12. Olin, P. (1991), *Dev. Biol Stand.* 73, 33–36.

13. Zealey, G., et al. (1992), *Vaccine Research* 1, 413–427.

14. Pizza, M., et al. (1989), *Science* 246, 497–499.

15. Loosmore, S., et al. (1990), *Infect. Immun.* 58, 3653–3662.

16. Locht, C. and Keith, J. (1986), *Science* 232, 1258–1264.

17. Cieplak, W., et al. (1988), *Proc. Natl. Acad. Sci. USA* 85, 4667–4671.

18. Burnette, W., et al. (1988), *Science* 242, 72–74.

19. Kaslow, H., et al. (1992), *Vaccine Res.* 1, 47–54.

20. Cockle, S. (1989), *FEBS Letters* 249, 329–332.

21. Lobet, Y., et al. (1993), *J. Exp. Med.* 177, 79–87.

22. Loosmore, S., et al. (1993), *Infect. Immun.* 61, 2316–2324.

23. Choe, S., et al. (1992), *Nature* 357, 216–222.

24. Allured, V., et al. (1986), *Proc. Natl. Acad. Sci. U.S.A.* 83, 1320–1324.

25. Brandhuber, B. et al. (1988) *Proteins* 3, 146–154

26. Sixma, T., et al. (1991), *Nature* 351, 371–377.

27. Sixma, T., et al. (1993), *J. Mol. Biol.* 230, 8990–9180.

28. Sixma, T., et al. (1993), *Biochemistry* 32, 191–198.

29. Stein, P., et al. (1992), *Nature* 355, 748–750.

30. Wont, J. et al. (1992), *Infect. Immun.* 60, 3303–3308

31. Graf. R. et al. (1992) *Molec. Pharmacol.,* 42, 760–764

32. Spangler, B., et al. (1988), *International Workshop on Bordetella pertussis*, Rocky Mountain Laboratories, Hamilton, Mont.

33. Raghavan, M., et al. (1990), *J. Molec. Biol.* 213, 411–414.

34. Sakabe, N. (1983), *J. Appl. Crystallogr.* 16, 542–547.

35. Higashi, T. (1989), *J. Appl. Crystallogr.* 22, 9–18.

36. Sheldrick, G. (1991), in *Crystallographic Computing 5: From Chemistry to Biology* (eds Moras, D., et al.) pp. 145–157 (Oxford University Press, Oxford).

37. Otwinowski, Z. (1991), in *Isomorphous Replacement and Anomalous Scattering: Proceedings of the CCP4 Study Weekend 25–26 January 1991* (eds Wolf, W., Evans, P. and Leslie, A.) pp.80–86 (SERC, Daresbury Laboratory).

38. Colman, P. et al. (1976), in *Crystallographic Computing Techniques* (eds Ahmed, F., Huml, Y, and Sedlacek, B.) pp. 248–258 (Munksgaard, Copenhagen).

39. Read, R. and Schierbeek, K. (1988), *J Appl. Crystallogr.* 21, 490–495.

40. Podjarny, A. and Rees, B. (1991), in *Crystallographic Computing 5: From Chemistry to Biology* (eds Moras, D., Podjarny, A. and Thierry, J.) pp.361–372 (Oxford University Press, Oxford).

41. Jones, T., et al. (1991), *Acta Crystallogr.* A47, 110–119.

42. Brünger, A., et al. (1987), *Science* 235, 458–460.

43. Read, R. (1986), *Acta Crystallogr.* A42, 140–149.

44. Loosmore, S., et al. (1989), *Nucleic Acids Research* 17, 8365.

45. Morris, A., et al. (1992), *Proteins* 12, 345–364.

46. Kabsch, W. and Sander, C. (1983), *Biopolymers* 22, 2577–2637.

47. Pizza, M., et al. (1988), *Proc. Natl. Acad. Sci. U.S.A.* 85, 7521–7525.

48. Barbieri, J. and Cortina, G. (1988), *Infect. Immun.* 56, 1934–1941.

49. Janin, J., et al. (1988), *J. Molec. Biol.* 204, 155–164.

50. Krueger, K., et al. (1991), *J. Biol. Chem.* 266, 8122–8128.

51. Murzin, A., (1993), *EMBO J.* 12, 861–867.

52. Tamura, M., et al. (1982), *Biochemistry* 21, 5516–5522.

53. Weis, W., et al. (1991), *Science* 254, 1608–1615.

54. Weis, W., et al. (1992), *Nature* 360, 127–134.

55. Heerze, L., et al. (1992), *J. Biol. Chem.* 267, 25810–25815.

56. Wright, C. (1990), *J. Molec. Biol.* 215, 635–651.

57. Cortina, G. and Barbieri J. (1991), *J. Biol. Chem.* 266, 3022–3030.

58. Klein, P., et al. (1985), *Biochim. Biophys. Acta* 815, 468–476.

59. Weis, W. et al. (1990) *J. Molec. Biol.* 212, 737–761.

60. Breg, J. (1989) *Eur. J. Biochem.* 178, 727–739.

61. Shigeta R. (1994) *Acta Crystallagr* D50, 71–74

62. Armstrong, G. and Peppler M. (1987), *Infect. Immun.* 55, 1294–1299.

63. Allen, F. (1973), *Cambridge Crystallagraphic Data Center.* 2. Structural Data File K. Chem. Doc. 13, 119.

64. Kaslow, H., et al. (1989), *J. Biol. Chem.* 264, 6386–6390.

65. Zealey, G. et al. (1990) *Biol. Tech.* 8, 1025–1029.

66. Zealey, G. et al. (1992) *Appl. Environ. Microbiol.* 58, 208–214.

67. Krueger, K. M. and Barbieri, J. T. (1993), *J. Biol. Chem.* 268, 12570–12578.

68. Ditta, G., T. Schmidhauser, E. Yakobson, P. Lu, X.-W. Liang, D. r. Finlay, D. Guiney, and D. R. Helinski (1985) Plasmid 13:149–153

What we claim is:

1. A method of preparing a pertussis holotoxin having a modified biological activity, which comprises:

(A) identifying at least one site in a pertussis holotoxin that interacts with the molecule that is capable of forming a complex with the holotoxin and which molecule is an effector molecule which is an adenine nucleotide and which site contributes to toxicity, cell binding or enzymatic activity of pertussis holotoxin by (a) forming a crystalline complex between at least a portion of pertussis holotoxin which is pertussis holotoxin, an analog thereof, a subunit, a portion of a subunit or a combination of subunits and said molecule, including exposing crystals of the at least a portion of the holotoxin to the molecule, under conditions to effect formation of the crystalline complex without substantial disruption of the crystals;

(b) determining the three-dimensional structure of the complex by X-ray crystallography;

(c) analyzing the structure to identify the at least one interacting site; and (B) modifying said identified at least one site to alter the toxicity, cell binding or enzyme activity of said pertassis holotoxin.

2. The method of claim 1, wherein the adenine nucleotide is ATP.

3. A method of preparing a pertussis holotoxin having a modified biological activity, which comprises:

(A) identifying at least one site in pertussis holotoxin that interacts with a molecule that is capable of forming a complex with the holotoxin and which molecule is a substrate which is a GTP-binding protein, an α-subunit of a GTP-binding protein, or a (C-terminal fragment of an α-subunit of a GTP-binding protein and which site contributes to toxicity, cell binding or enzymatic activity of pertussis holotoxin by:

(a) forming a crystalline complex between at least a portion of pertussis holotoxin which is pertussis holotoxin, an analog thereof, a subunit, a position of a subunit or a combination of subunits and said molecule, including exposing crystals of the at least a portion of the holotoxin to the molecule, under conditions to effect formation of the crystalline complex without substantial disruption of the crystals;

(b) determining the three-dimensional structure of the complex by X-ray crystallography; and (c) analysing the structure to identify the at least one interacting site; and (B) modifying said identified at least one site to alter the toxicity, cell binding or enzymatic activity of said pertussis holotoxin.

4. The method of claim 3, wherein the GTP-binding protein is selected from the group consisting of $G_i$, $G_o$, and transducin.

5. A method of preparing a pertussis holotoxin having a modified biological activity, which comprises:

(A) identifying at least one site in pertussis holotoxin that interacts with molecule that is capable of forming a complex with the holotoxin and which molecule is a substrate which is NM or a substantially non-hydrolysable analog of NAD and which site contributes to toxicity, cell binding or enzymatic activity of pertussis holotoxin by:

(a) forming a crystalline complex between at least a portion of pertussis holotoxin which is pertussis holotoxin, an analog thereof, a subunit, a portion of a subunit or a combination of subunits and said molecule, including exposing crystals of the at least a portion or the holotoxin to the molecule, under conditions to effect formation of the crystalline complex without substantial disruption of the crystals;

(b) determining the three-dimensional structure of the complex by X-ray crystallography;

(c) analyzing the structure to identify the at least one interacting site; and (B) modifying said identified at least one site to alter the toxicity, cell binding or enzymatic activity of said pertussis holotoxin.

\* \* \* \* \*

UNITED STATES PATENT AND TRADEMARK OFFICE
CERTIFICATE OF CORRECTION

PATENT NO.    : 5,856,122
DATED         : January 5, 1999
INVENTOR(S)   : Read, et al It is certified that error appears in the above-identified patent and that said Letters Patent is hereby corrected as shown below:

On the title page, item [73] should read -- Connaught Laboratories Limited and University of Alberta, Edmonton, Canada --

Signed and Sealed this

Thirty-first Day of October, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Val  Tyr  Arg  Tyr  Asp  Ser
    1                      5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Phe  Val  Ser  Thr  Ser  Ser  Ser  Arg  Arg  Tyr  Thr  Glu
    1                      5                                    1 0

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Phe  Ile  Gly  Tyr  Ile  Tyr  Glu  Val  Arg
    1                      5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Ser  Glu  Tyr  Leu  Ala  His  Arg
    1                      5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Asn  Ile  Arg  Arg  Val
    1                      5

( 2 ) INFORMATION FOR SEQ ID NO:6:

(i) SEQUENCE CHARACTERISTICS:
    (A) LENGTH: 6 amino acids
    (B) TYPE: amino acid
    (C) STRANDEDNESS: single
    (D) TOPOLOGY: linear (xi) SEQUENCE DESCRIPTION: SEQ ID NO:6:

Leu Tyr Arg Ala Asp Ser
 1               5

(2) INFORMATION FOR SEQ ID NO:7:

(i) SEQUENCE CHARACTERISTICS:
    (A) LENGTH: 12 amino acids
    (B) TYPE: amino acid
    (C) STRANDEDNESS: single
    (D) TOPOLOGY: linear (xi) SEQUENCE DESCRIPTION: SEQ ID NO:7:

Tyr Val Ser Thr Ser Leu Ser Leu Arg Ser Ala His
 1               5                   1 0

(2) INFORMATION FOR SEQ ID NO:8:

(i) SEQUENCE CHARACTERISTICS:
    (A) LENGTH: 9 amino acids
    (B) TYPE: amino acid
    (C) STRANDEDNESS: single
    (D) TOPOLOGY: linear (xi) SEQUENCE DESCRIPTION: SEQ ID NO:8:

Ser Thr Tyr Tyr Ile Tyr Val Ile Ala
 1               5

(2) INFORMATION FOR SEQ ID NO:9:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:9:

Gln Glu Val Ser Ala Leu Gly
 1               5

(2) INFORMATION FOR SEQ ID NO:10:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:10:

Gln Ile Tyr Gly Trp
 1               5

(2) INFORMATION FOR SEQ ID NO:11:

(i) SEQUENCE CHARACTERISTICS:
    (A) LENGTH: 6 amino acids
    (B) TYPE: amino acid
    (C) STRANDEDNESS: single
    (D) TOPOLOGY: linear (xi) SEQUENCE DESCRIPTION: SEQ ID NO:11:

Gly Tyr His Gly Thr Phe
 1               5

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Gly Phe Tyr Ile Ala Gly Asp Pro Ala Leu Ala Tyr
 1               5                  10
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

```
Arg Asn Gly Ala Leu Leu Arg Val Tyr
 1               5
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Leu Glu Thr Ile Leu Gly Trp
 1               5
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Val Val Ile Pro Ser
 1               5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Ser Tyr His Gly Thr Lys
 1               5
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

Gly Phe Tyr Ser Thr Asp Asn Lys Tyr Asp Ala Ala
 1               5                  10

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

Lys Ala Gly Gly Val Val Lys Val Thr
 1               5

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

Val Glu Tyr Ile Asn Asn Trp
 1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

Ser Val Glu Leu Glu
 1               5

( 2 ) INFORMATION FOR SEQ ID NO:21:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

Thr Pro Asp Cys Val Thr Gly Lys Val Glu Tyr Thr Lys Tyr Asn Asp
 1               5                  10                      15

Asp Asp Thr Phe Thr Val Lys Val Gly Asp Lys Glu Leu Phe Thr Asn
                 20                  25                  30

Arg Trp Asn Leu Gln Ser Leu Leu Leu Ser Ala Gln Ile Thr Gly Met
             35                  40                  45

Thr Val Thr Ile Lys Thr Asn Ala Cys His Asn Gly Gly Gly Phe Ser
         50                  55                  60

Glu Val Ile Phe Arg
 65

( 2 ) INFORMATION FOR SEQ ID NO:22:

( i ) SEQUENCE CHARACTERISTICS:
        ( A ) LENGTH: 104 amino acids
        ( B ) TYPE: amino acid
        ( C ) STRANDEDNESS: single -continued (D) TOPOLOGY: linear (xi) SEQUENCE DESCRIPTION: SEQ ID NO:22:

| Gln | Pro | Ala | Thr | Asp | His | Tyr | Tyr | Ser | Asn | Val | Thr | Ala | Thr | Arg | Leu |
|---|---|---|---|---|---|---|---|---|---|---|---|---|---|---|---|
| 1 | | | | 5 | | | | | 10 | | | | | 15 | |

| Leu | Ser | Ser | Thr | Asn | Ser | Arg | Leu | Cys | Ala | Val | Phe | Val | Arg | Ser | Gly |
|---|---|---|---|---|---|---|---|---|---|---|---|---|---|---|---|
| | | | 20 | | | | | 25 | | | | | 30 | | |

| Gln | Pro | Val | Ile | Gly | Ala | Cys | Thr | Ser | Pro | Tyr | Asp | Gly | Lys | Tyr | Trp |
|---|---|---|---|---|---|---|---|---|---|---|---|---|---|---|---|
| | | | 35 | | | | | 40 | | | | | 45 | | |

| Ser | Met | Tyr | Ser | Arg | Leu | Arg | Lys | Met | Leu | Tyr | Leu | Ile | Tyr | Val | Ala |
|---|---|---|---|---|---|---|---|---|---|---|---|---|---|---|---|
| | 50 | | | | | 55 | | | | | 60 | | | | |

| Gly | Ile | Ser | Val | Arg | Val | His | Val | Ser | Lys | Glu | Glu | Gln | Tyr | Tyr | Asp |
|---|---|---|---|---|---|---|---|---|---|---|---|---|---|---|---|
| 65 | | | | | 70 | | | | | 75 | | | | | 80 |

| Tyr | Glu | Asp | Ala | Thr | Phe | Glu | Thr | Tyr | Ala | Leu | Thr | Gly | Ile | Ser | Ile |
|---|---|---|---|---|---|---|---|---|---|---|---|---|---|---|---|
| | | | | 85 | | | | | 90 | | | | | 95 | |

| Cys | Asn | Pro | Gly | Ser | Ser | Leu | Cys |
|---|---|---|---|---|---|---|---|
| | | | 100 | | | | |

(2) INFORMATION FOR SEQ ID NO:23:

(i) SEQUENCE CHARACTERISTICS:
(A) LENGTH: 104 amino acids
(B) TYPE: amino acid
(C) STRANDEDNESS: single
(D) TOPOLOGY: linear (xi) SEQUENCE DESCRIPTION: SEQ ID NO:23:

| Gln | Pro | Ala | Ala | Asp | His | Tyr | Tyr | Ser | Lys | Val | Thr | Ala | Thr | Arg | Leu |
|---|---|---|---|---|---|---|---|---|---|---|---|---|---|---|---|
| 1 | | | | 5 | | | | | 10 | | | | | 15 | |

| Leu | Ala | Ser | Thr | Asn | Ser | Arg | Leu | Cys | Ala | Val | Phe | Val | Arg | Asp | Gly |
|---|---|---|---|---|---|---|---|---|---|---|---|---|---|---|---|
| | | | 20 | | | | | 25 | | | | | 30 | | |

| Gln | Ser | Val | Ile | Gly | Ala | Cys | Ala | Ser | Pro | Tyr | Glu | Gly | Arg | Tyr | Arg |
|---|---|---|---|---|---|---|---|---|---|---|---|---|---|---|---|
| | | | 35 | | | | | 40 | | | | | 45 | | |

| Asp | Met | Tyr | Asp | Ala | Leu | Arg | Arg | Leu | Leu | Tyr | Met | Ile | Tyr | Met | Ser |
|---|---|---|---|---|---|---|---|---|---|---|---|---|---|---|---|
| | 50 | | | | | 55 | | | | | 60 | | | | |

| Gly | Leu | Ala | Val | Arg | Val | His | Val | Ser | Lys | Glu | Glu | Gln | Tyr | Tyr | Asp |
|---|---|---|---|---|---|---|---|---|---|---|---|---|---|---|---|
| 65 | | | | | 70 | | | | | 75 | | | | | 80 |

| Tyr | Glu | Asp | Ala | Thr | Phe | Gln | Thr | Tyr | Ala | Leu | Thr | Gly | Ile | Ser | Leu |
|---|---|---|---|---|---|---|---|---|---|---|---|---|---|---|---|
| | | | | 85 | | | | | 90 | | | | | 95 | |

| Cys | Asn | Pro | Ala | Ala | Ser | Ile | Cys |
|---|---|---|---|---|---|---|---|
| | | | 100 | | | | |

(2) INFORMATION FOR SEQ ID NO:24:

(i) SEQUENCE CHARACTERISTICS:
(A) LENGTH: 110 amino acids
(B) TYPE: amino acid
(C) STRANDEDNESS: single
(D) TOPOLOGY: linear (xi) SEQUENCE DESCRIPTION: SEQ ID NO:24:

| Asp | Val | Pro | Tyr | Val | Leu | Val | Lys | Thr | Asn | Met | Val | Val | Thr | Ser | Val |
|---|---|---|---|---|---|---|---|---|---|---|---|---|---|---|---|
| 1 | | | | 5 | | | | | 10 | | | | | 15 | |

| Ala | Met | Lys | Pro | Tyr | Glu | Val | Thr | Pro | Thr | Arg | Met | Leu | Val | Cys | Gly |
|---|---|---|---|---|---|---|---|---|---|---|---|---|---|---|---|
| | | | 20 | | | | | 25 | | | | | 30 | | |

| Ile | Ala | Ala | Lys | Leu | Gly | Ala | Ala | Ala | Ser | Ser | Pro | Asp | Ala | His | Val |
|---|---|---|---|---|---|---|---|---|---|---|---|---|---|---|---|
| | | | 35 | | | | | 40 | | | | | 45 | | |

| Pro | Phe | Cys | Phe | Gly | Lys | Asp | Leu | Lys | Arg | Pro | Gly | Ser | Ser | Pro | Met |
|---|---|---|---|---|---|---|---|---|---|---|---|---|---|---|---|
| | | | | 50 | | | | | 55 | | | | | 60 | |

```
Glu  Val  Met  Leu  Arg  Ala  Val  Phe  Met  Gln  Gln  Arg  Pro  Leu  Arg  Met
 65                 70                  75                       80

Phe  Leu  Gly  Pro  Lys  Gln  Leu  Thr  Phe  Glu  Gly  Lys  Pro  Ala  Leu  Glu
                85                  90                       95

Leu  Ile  Arg  Asn  Val  Glu  Cys  Ser  Gly  Lys  Gln  Asp  Cys  Pro
               100                 105                      110
```

( 2 ) INFORMATION FOR SEQ ID NO:25:

( i ) SEQUENCE CHARACTERISTICS:
        ( A ) LENGTH: 99 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

```
Gly  Leu  Pro  Thr  His  Leu  Tyr  Lys  Asn  Phe  Thr  Val  Gln  Glu  Leu  Ala
  1                  5                  10                       15

Leu  Lys  Leu  Lys  Gly  Lys  Asn  Gln  Glu  Phe  Cys  Leu  Thr  Ala  Phe  Met
                20                  25                       30

Ser  Gly  Arg  Ser  Leu  Val  Arg  Ala  Cys  Leu  Ser  Asp  Ala  Gly  His  Glu
                35                  40                       45

His  Asp  Thr  Trp  Phe  Asp  Thr  Met  Leu  Gly  Phe  Ala  Ile  Ser  Ala  Tyr
          50                      55                       60

Ala  Leu  Lys  Ser  Arg  Ile  Ala  Leu  Thr  Val  Glu  Asp  Ser  Pro  Tyr  Pro
 65                 70                  75                       80

Gly  Thr  Pro  Gly  Asp  Leu  Leu  Glu  Leu  Gln  Ile  Cys  Pro  Leu  Asn  Gly
               85                   90                       95

Tyr  Cys  Glu
```

( 2 ) INFORMATION FOR SEQ ID NO:26:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

```
Glu  Tyr  Arg  Asn  Thr  Gln  Ile  Tyr  Thr  Ile  Asn  Asp  Lys  Ile  Leu  Ser
  1                  5                  10                       15

Tyr  Thr  Glu  Ser  Met  Ala  Gly  Lys  Arg  Glu  Met  Val  Ile  Ile  Thr  Phe
                20                  25                       30

Lys  Ser  Gly  Glu  Thr  Phe  Gln  Val  Glu  Val  Pro  Gly  Ser  Gln  His  Ile
                35                  40                       45

Asp  Ser  Gln  Lys  Lys  Ala  Ile  Glu  Arg  Met  Lys  Asp  Thr  Leu  Arg  Ile
          50                      55                       60

Thr  Tyr  Leu  Thr  Glu  Thr  Lys  Ile  Asp  Lys  Leu  Cys  Val  Trp  Asn  Asn
 65                 70                  75                       80

Lys  Thr  Pro  Asn  Ser  Ile  Ala  Ala  Ile  Ser  Met  Lys  Asn
               85                   90
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:27:

```
       Asn Lys Thr Arg Ala Leu
         1               5
```

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:28:

```
   Ser Gly Asp Leu Gln Glu Tyr Leu Arg His Val Thr Arg
     1               5                  10
```

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:29:

```
   Ser Ile Phe Ala Leu
     1               5
```

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:30:

```
   Asp Gly Thr Tyr Leu
     1               5
```

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:31:

```
   Tyr Gly Gly Val Ile Lys Asp
     1               5
```

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:32:

```
   Thr Thr Phe Cys Ile Met
     1               5
```

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( C ) STRANDEDNESS: single (D) TOPOLOGY: linear (x i) SEQUENCE DESCRIPTION: SEQ ID NO:33:

Asn Gly Thr Arg Ala Leu
1               5

(2) INFORMATION FOR SEQ ID NO:34:

(i) SEQUENCE CHARACTERISTICS:
(A) LENGTH: 13 amino acids
(B) TYPE: amino acid
(C) STRANDEDNESS: single
(D) TOPOLOGY: linear (x i) SEQUENCE DESCRIPTION: SEQ ID NO:34:

Asn Ala Glu Leu Gln Thr Tyr Leu Arg Gln Ile Thr Pro
1               5                   10

(2) INFORMATION FOR SEQ ID NO:35:

(i) SEQUENCE CHARACTERISTICS:
(A) LENGTH: 5 amino acids
(B) TYPE: amino acid
(C) STRANDEDNESS: single
(D) TOPOLOGY: linear (x i) SEQUENCE DESCRIPTION: SEQ ID NO:35:

Ser Ile Tyr Gly Leu
1               5

(2) INFORMATION FOR SEQ ID NO:36:

(i) SEQUENCE CHARACTERISTICS:
(A) LENGTH: 5 amino acids
(B) TYPE: amino acid
(C) STRANDEDNESS: single
(D) TOPOLOGY: linear (x i) SEQUENCE DESCRIPTION: SEQ ID NO:36:

Asp Gly Thr Tyr Leu
1               5

(2) INFORMATION FOR SEQ ID NO:37:

(i) SEQUENCE CHARACTERISTICS:
(A) LENGTH: 7 amino acids
(B) TYPE: amino acid
(C) STRANDEDNESS: single
(D) TOPOLOGY: linear (x i) SEQUENCE DESCRIPTION: SEQ ID NO:37:

Tyr Gly Gly Ile Ile Lys Asp
1               5

(2) INFORMATION FOR SEQ ID NO:38:

(i) SEQUENCE CHARACTERISTICS:
(A) LENGTH: 6 amino acids
(B) TYPE: amino acid
(C) STRANDEDNESS: single
(D) TOPOLOGY: linear (x i) SEQUENCE DESCRIPTION: SEQ ID NO:38:

Glu Thr Phe Cys Ile Thr
1               5

(2) INFORMATION FOR SEQ ID NO:39:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( x i ) SEQUENCE DESCRIPTION: SEQ ID NO:39:

Leu Arg Gly Thr Val Ala
 1       5

( 2 ) INFORMATION FOR SEQ ID NO:40:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( x i ) SEQUENCE DESCRIPTION: SEQ ID NO:40:

Asn Ala Glu Glu Asn Lys Ala Ile Gln Glu Val Ala Lys
 1       5          10

( 2 ) INFORMATION FOR SEQ ID NO:41:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:41:

Thr Ser Ala Phe Leu
 1      5

( 2 ) INFORMATION FOR SEQ ID NO:42:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:42:

Cys Val Thr Ile Val
 1      5

( 2 ) INFORMATION FOR SEQ ID NO:43:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:43:

Asp Asn Gly Leu Trp Asn Asp
 1       5

( 2 ) INFORMATION FOR SEQ ID NO:44:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( x i ) SEQUENCE DESCRIPTION: SEQ ID NO:44:

Thr Ala Val Cys Glu Phe
 1       5

( 2 ) INFORMATION FOR SEQ ID NO:45:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:45:

```
Ala  Met  Ala  Ala  Trp  Ser  Glu  Arg  Ala  Gly
 1                   5                        10
```

( 2 ) INFORMATION FOR SEQ ID NO:46:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:46:

```
Val  Ala  Ser  Ile  Val  Gly  Thr  Leu  Val  Arg  Met  Ala  Pro  Val  Ile  Gly
 1                   5                        10                            15
Ala  Cys  Met  Ala
                20
```